(12) United States Patent
Onda et al.

(10) Patent No.: US 7,283,869 B2
(45) Date of Patent: Oct. 16, 2007

(54) APPARATUS FOR MEASURING BODY FAT

(75) Inventors: Tomohiro Onda, Tokyo (JP);
Mitsuhiro Katashima, Tokyo (JP);
Junichi Nojima, Tochigi (JP); Susumu Fujinami, Tokyo (JP); Kazuhiro Tashiro, Tokyo (JP)

(73) Assignee: Kao Corporation, Tokyo (JP)

( * ) Notice: Subject to any disclaimer, the term of this patent is extended or adjusted under 35 U.S.C. 154(b) by 422 days.

(21) Appl. No.: 10/468,013

(22) PCT Filed: Feb. 15, 2002

(86) PCT No.: PCT/JP02/01325

§ 371 (c)(1),
(2), (4) Date: Aug. 22, 2003

(87) PCT Pub. No.: WO02/065900

PCT Pub. Date: Aug. 29, 2002

(65) Prior Publication Data

US 2004/0077969 A1 Apr. 22, 2004

(30) Foreign Application Priority Data

Feb. 22, 2001 (JP) .............................. 2001-046661
Apr. 13, 2001 (JP) .............................. 2001-115607
Jul. 6, 2001 (JP) .............................. 2001-206937

(51) Int. Cl.
*A61B 5/05* (2006.01)
(52) U.S. Cl. ...................................................... 600/547
(58) Field of Classification Search ................ 600/547, 600/587
See application file for complete search history.

(56) References Cited

U.S. PATENT DOCUMENTS 3,998,213 A * 12/1976 Price .......................... 600/383
4,328,814 A * 5/1982 Arkans ........................ 600/393

(Continued)

FOREIGN PATENT DOCUMENTS

GB 2 160 323 12/1985

(Continued)

OTHER PUBLICATIONS

Katsuyuki Sakamoto: "An Impedance CT method" Japanese Society For Medical and Biological Engineering, vol. 8, No. 8, pp. 49-56 1994 (with English abstract).

*Primary Examiner*—Max F. Hindenburg
*Assistant Examiner*—Brian Szmal
(74) *Attorney, Agent, or Firm*—Oblon, Spivak, McClelland, Maier & Neustadt, P.C.

(57) ABSTRACT

An apparatus has a first electrode group (1) including at least one electrode and arranged on the abdominal surface of a subject (human) with the navel of the subject serving as a reference position, a second electrode group (2) including at least one electrode and arranged on the back surface of the subject, a third electrode group (3) including at least two electrodes and arranged on the surface of the subject at an intermediate position between the first and second electrode groups (1, 2), and a controller (8) to supply a current between an electrode selected from the first electrode group (1) and an electrode selected from the second electrode group (2), measure a voltage generated between two electrodes of the third electrode group (3), and compute an abdominal fat quantity of the subject according to the measured voltage.

39 Claims, 21 Drawing Sheets

U.S. PATENT DOCUMENTS

| | | | |
|---|---|---|---|
| 5,216,817 A * | 6/1993 | Misevich et al. | 33/515 |
| 5,293,867 A * | 3/1994 | Oommen | 600/300 |
| 5,335,667 A * | 8/1994 | Cha et al. | 600/547 |
| 5,484,668 A * | 1/1996 | Kutz et al. | 429/121 |
| 5,685,303 A * | 11/1997 | Rollman et al. | 600/390 |
| 6,577,897 B1 * | 6/2003 | Shurubura et al. | 600/547 |
| 6,978,170 B1 * | 12/2005 | Onda et al. | 600/547 |
| 2001/0020138 A1 * | 9/2001 | Ishigooka et al. | 600/547 |
| 2001/0034491 A1 * | 10/2001 | Benson et al. | 600/547 |
| 2003/0050570 A1 * | 3/2003 | Kodama | 600/547 |

FOREIGN PATENT DOCUMENTS

| | | | |
|---|---|---|---|
| JP | 10-510455 | | 10/1998 |
| JP | 09-276838 | * | 4/1999 |
| JP | 11 113870 | | 4/1999 |
| JP | 110113870 | * | 4/1999 |
| JP | 11-123182 | | 5/1999 |
| JP | 11-309123 | | 11/1999 |
| JP | 2000 014655 | | 1/2000 |
| JP | 2000 175875 | * | 6/2000 |
| JP | 2000-225100 | | 8/2000 |
| JP | 2000-350710 | | 12/2000 |
| JP | 2000-350727 | | 12/2000 |
| JP | 2001-104271 | | 4/2001 |
| JP | 2001-190513 | | 7/2001 |
| JP | 2001-212111 | | 8/2001 |
| JP | 2001-286452 | | 10/2001 |
| WO | 99 65395 | | 12/1999 |

* cited by examiner

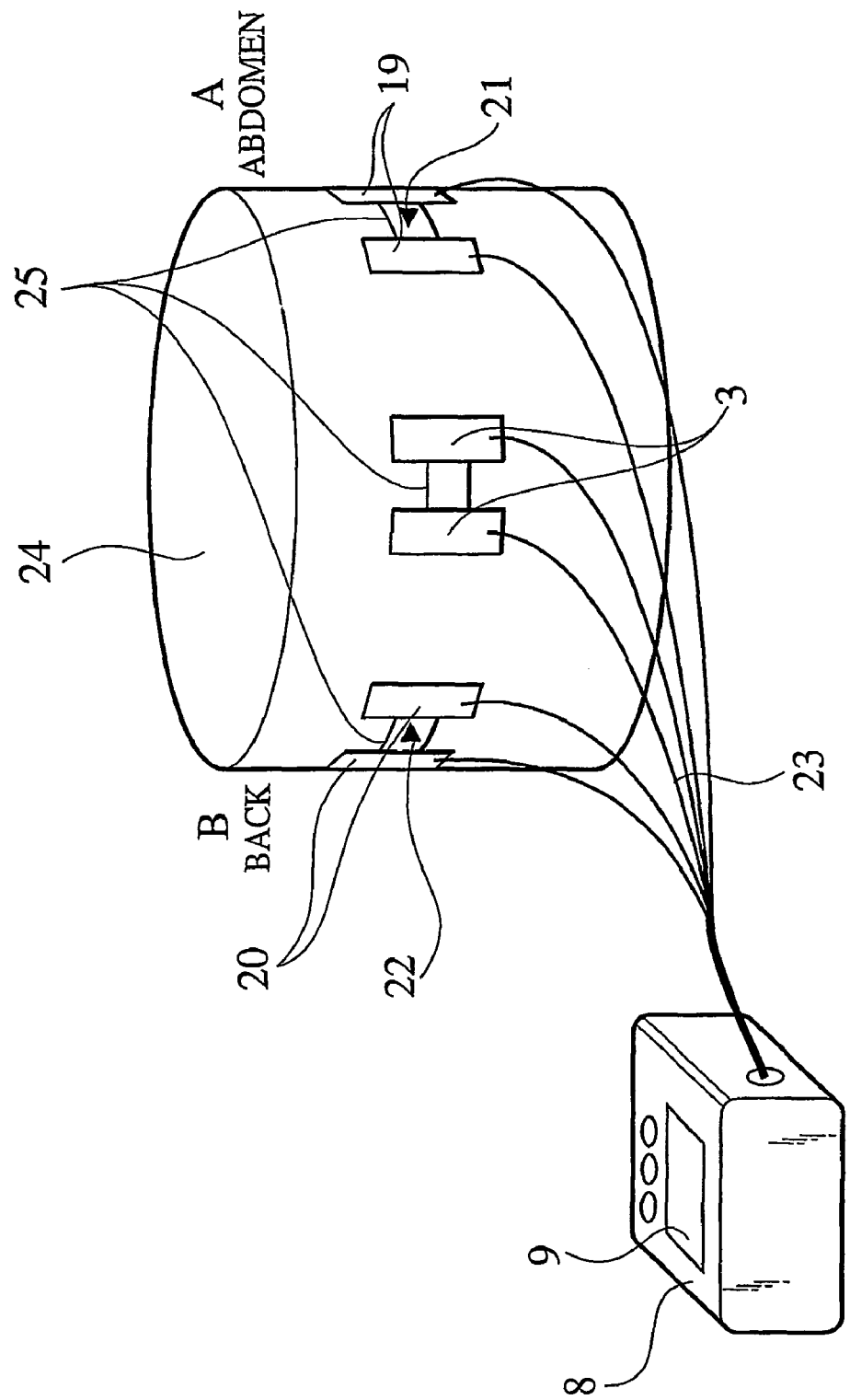

APPARATUS FOR MEASURING BODY FAT

TECHNICAL FIELD

The present invention relates to a method of and an apparatus for easily and accurately measuring a subcutaneous fat quantity and a visceral fat quantity of a human body.

BACKGROUND ART

An impedance CT system employs the fact that media have individual electric impedance values, to find spatial distributions of media in a three-dimensional object. The impedance CT system passes a current through an object, measures a potential distribution induced at the surface of the object, and visualizes an impedance distribution inside the object according to the potential distribution. The system is applicable to measure the distributions of blood, lungs, fat, etc., in a human body as described in a bulletin Bio Medical Engineering (BME) Vol. 8, No. 8 (1994), p. 49, issued by Japanese Society for Medical and Biological Engineering.

In addition to the impedance CT system, there are other apparatuses to measure electric impedance values and find subcutaneous and visceral fat quantities. An example of such apparatuses is a body fat measuring apparatus disclosed in Japanese Patent Laid Open Publication No. 11-113870 (referred to as "related art 1"). Another example is an internal fat measuring instrument disclosed in Japanese Patent Laid Open Publication No. 11-123182 (referred to as "related art 2"). The related art 1 attaches a plurality of electrodes to the surface of a subject (human), measures impedance values among the electrodes, and creates an impedance matrix for a cross section of the subject defined by the attached electrodes. An operation unit of the related art 1 calculates the product of the impedance matrix and a coefficient matrix prepared from information on the electrodes attached part of the subject entered through an input unit, and according to the product, provides a cross sectional body fat distribution of the subject. The related art 2 winds a belt around the body of a subject. The inside of the belt has electrode pairs each consisting of a current path forming electrode and a measuring electrode. The electrode pairs are arranged substantially at regular intervals. Two electrode pairs are chosen, and an AC current is passed between the current path forming electrodes of the chosen electrode pairs, to form a current path. The measuring electrodes measure an impedance value in the current path. The two electrode pairs are properly chosen so that adjacent electrodes may mainly measure subcutaneous fat and opposing electrodes may mainly measure visceral fat.

DISCLOSURE OF INVENTION

The apparatus that measures body fat with the impedance CT system involves an insufficient spatial resolution to estimate an internal fat distribution, and therefore, is insufficient to correctly calculate a body fat quantity. In addition, the apparatus must carry out many numerical calculations to find a body fat quantity.

The related art 1 provides no concrete description how to form a coefficient matrix for electrodes attached part and how to create a cross sectional body fat distribution image from the product of impedance and coefficient matrixes.

The related art 2 may measure a subcutaneous fat quantity of a subject. The measured fat quantity, however, includes the influence of the quantities and distributions of other media in the subject, and therefore, is inaccurate. In addition, the related art 2 is incapable of correctly measuring the visceral fat of a subject due to the strong influence of a subcutaneous fat layer of the subject.

The present invention provides a body fat measuring apparatus easy to install on a human body and capable of easily and correctly measuring the quantity, such as thickness and cross sectional area, of layered subcutaneous fat as well as the quantity of visceral fat of a human body.

According to a first aspect of the present invention, a body fat measuring apparatus has a first electrode group including at least an electrode and arranged on the abdominal surface of a subject with the navel of the subject serving as a reference position, a second electrode group including at least an electrode and arranged on the back surface of the subject, a third electrode group including at least two electrodes and arranged on the surface of the subject substantially at an intermediate position between the first and second electrode groups, a measuring unit to supply a current between an electrode selected from the first electrode group and an electrode selected from the second electrode group and measure a voltage generated between two electrodes of the third electrode group, and a computing unit to compute an abdominal fat quantity of the subject according to the measured voltage.

According to a second aspect of the present invention, a body fat measuring apparatus has a first electrode group including at least an electrode and arranged on the abdominal surface of a subject with the navel of the subject serving as a reference position, a second electrode group including at least three electrodes and arranged on the back surface of the subject, a measuring unit to supply a current between two electrodes selected from the second electrode group and measure a voltage generated between an electrode selected from the first electrode group and an electrode selected from the second electrode group, and a computing unit to compute an abdominal fat quantity of the subject according to the measured voltage.

The apparatus of any one of the aspects may improve the accuracy of abdominal fat computations of a subject by considering a circumferential length of the body, the sex and/or age of the subject.

According to a third aspect of the present invention, a body fat measuring belt has a navel marker to be aligned with the navel of a subject, a first electrode group including at least an electrode and arranged on the abdominal surface of the subject with the navel of the subject serving as a reference position with which the navel marker is aligned, a second electrode group including at least an electrode and arranged on the back surface of the subject, and a third electrode group including at least two electrodes and arranged on the surface of the subject substantially at an intermediate position between the first and second electrode groups.

According to a fourth aspect of the present invention, a body fat measuring apparatus has two current supply electrodes arranged on the circumferential surface of a subject with the distance between the electrodes being sufficiently shorter than a circumferential length of the subject, a first measuring electrode arranged on the subject in the vicinity of one of the current supply electrodes, a second measuring electrode arranged on the subject substantially opposite to the current supply electrodes across the subject, a voltage measuring unit to supply a current between the current supply electrodes and measure a voltage generated between the first and second measuring electrodes, and a computing unit to compute a visceral fat quantity of the subject according to the measured voltage and a characteristic quantity representing the size of the subject.

In this specification, the "visceral fat quantity" collectively indicates the quantity of fat present inside a subject. Namely, the visceral fat quantity includes the quantity of visceral fat existing around internal organs of a subject and the quantity of general internal fat such as liver fat.

The "characteristic quantity" representing the size of a subject is a quantity that reflects the size of a cross sectional area of the subject, such as a total cross sectional area S at a given height of a subject, a circumferential length U around a cross section of the subject, a longitudinal width W1 between the abdomen and back of the subject, or a lateral width W2 between the flanks of the subject.

BRIEF DESCRIPTION OF DRAWINGS

FIG. 15 shows a body fat measuring apparatus according to a seventh modification based on the second embodiment;

BEST MODE FOR CARRYING OUT THE INVENTION

FIRST EMBODIMENT

Figure 1:
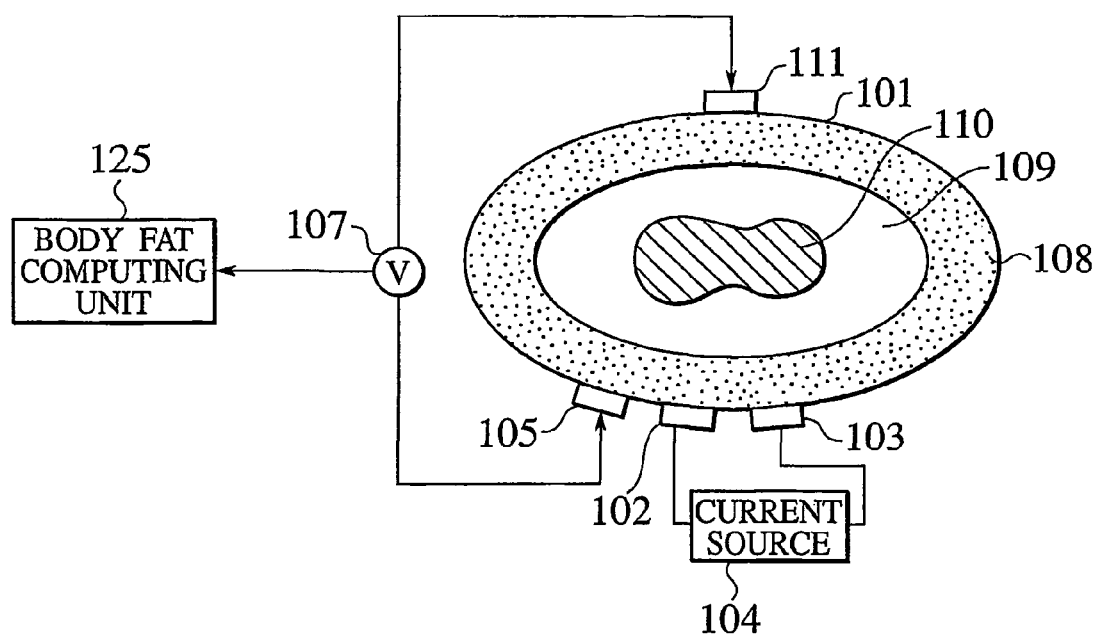
FIG. 1 shows a body fat measuring apparatus according to a first embodiment of the present invention.

FIG. 1 shows a body fat measuring apparatus according to the first embodiment of the present invention. The apparatus has two current supply electrodes 102 and 103 that are arranged on the surface of, for example, the body of a subject (human) 101. The distance between the electrodes 102 and 103 is sufficiently shorter than a circumferential length of the subject 101. The apparatus also has a current source 104 to supply a current between the electrodes 102 and 103, a first measuring electrode 105 arranged in the vicinity of the electrode 102, a second measuring electrode 111 arranged on the surface of the subject 101 substantially opposite to the electrodes 102 and 103 across the subject 101, a voltmeter 107 to measure a voltage generated between the electrodes 105 and 111, and a body fat computing unit 125 to compute a visceral fat quantity of the subject 101 according to the voltage measured by the voltmeter 107 and a characteristic quantity representing the size of the subject 101. The subject 101 has subcutaneous fat 108, nonfat part 109, whose impedance differs from that of the subcutaneous fat 108, and visceral fat 110, whose impedance differs from that of the nonfat part 109. The body fat computing unit 125 may be a computer.

A method of measuring a body fat quantity with the apparatus of FIG. 1 will be explained. The current source 104 supplies a current between the electrodes 102 and 103 that are arranged on a circumferential surface of the subject 101. The distance between the electrodes 102 and 103 is sufficiently shorter than the circumferential length of the subject 101. The voltmeter 107 measures a voltage generated between the first and second measuring electrodes 105 and 111. The electrode 105 is arranged close to the electrode 102, and the electrode 111 is arranged opposite to the electrodes 102 and 103 across the subject 101. The computing unit 125 computes a visceral fat quantity of, the subject 101 according to the measured voltage and a characteristic quantity representing the size of the subject 101.

The voltage V measured by the voltmeter 107 corresponds to the quantity of the subcutaneous fat 108, and the characteristic quantity representing the size of the subject 101 corresponds to the sum of the quantities of the subcutaneous fat 108 and visceral fat 110. The characteristic quantity is, for example, a total cross sectional area S of the subject 101, a circumferential length U around a cross section of the subject 101, a longitudinal width W1 between the abdomen and back of the subject 101, or a lateral width W2 between the flanks of the subject 101. Accordingly, a difference between the voltage V and the characteristic quantity representing the size of the subject 101 provides the quantity of the visceral fat 110. The positions of the electrodes 102, 103, and 105 on the subject 101 are determined to most correctly find the quantity of the visceral fat 110. For example, they are arranged on the back of the subject 101 where the quantity of the subcutaneous fat 108 is large.

The current source 104 may be of any one of DC and AC. If the current source 104 is an AC current source, a phase delay may simultaneously be measured when the voltmeter 107 measures a voltage, i.e., the amplitude or effective value of voltage. The measured phase delay is usable to analyze data. When measuring a human body, AC is easier to handle. The frequency of the AC current source may be 10 kHz to 500 kHz, preferably 50 kHz to 200 kHz, and a current value may be 0.3 mA to 3 mA.

To compute the quantity of the visceral fat 110, it is necessary to prepare a correlation expression that relates the voltage V measured by the voltmeter 107 and the characteristic quantity λ representing the size of the subject 101, such as a circumferential length U, to the quantity m of the visceral fat 110. To prepare such a correlation expression, a plurality of samples having different fat quantities are measured for voltage V, characteristic quantity λ, and visceral fat quantity m. When measuring the voltage V, the same current or different currents are applied to the samples. When different currents are used, measured voltages must be standardized based on one current. To measure the characteristic quantities of λ, measuring devices such as measuring tapes and scales are used. To measure the visceral fat quantities of m, tomographic images provided by an X-ray CT system or an MRI system are usable; based on the images, sectional areas and volumes serving as the visceral fat quantities are calculated. If the samples are not human bodies, they may be mechanically sliced to directly measure the sectional areas and volumes of visceral fat. The samples may be those having known internal structures. When calculating a sectional area from a tomographic image, current spreading may be considered. That is, not only the tomographic image of one section but also the tomographic images of the vicinities may be prepared, to calculate a visceral fat sectional area from an average of the tomographic images and this improves the correctness of the calculation.

The correlation expression mentioned above may be prepared from a multivariate analysis and approximated with a linear polynomial. For example, the correlation expression is as follows:

$$m = a0 + a1 \cdot \lambda^{\alpha} - a2 \cdot V \cdot \lambda'^{\beta},$$

where a0, a1, and a2 are regression coefficients, λ' is a characteristic quantity representing the size of the subject 101 and may be equal to λ, and α and β are exponents that are typically each 2 (α=β=2). The exponents α and β are not limited to 2 and are determined to provide an optimum correlation. If the characteristic quantities λ and λ' are each a circumferential length U of the subject 101, the correlation expression will be as follows:

$$m = a0 + a1 \cdot U^2 - a2 V \cdot U^2.$$

Once the correlation expression is established, the quantity m of the visceral fat 110 of the subject 101 is computed according to the voltage V measured with the voltmeter 107 and the characteristic quantity representing the size of the subject 101.

The distance between the current supply electrodes 102 and 103 is preferably less than 1/6, more preferably, 1/8 of the circumferential length of the subject 101. If the distance between the electrodes 102 and 103 is too large, the current supplied between them will flow deeply inside the subject 101. Then, the measured voltage V is affected by the distributions and quantities of the nonfat part 109 and visceral fat 110. If the distance between the electrodes 102 and 103 is too small, the measuring sensitivity of the apparatus will deteriorate for a subject 101 having a thick subcutaneous fat layer and the measured voltage V will be affected by the shapes and sizes of the electrodes.

The distance between the measuring electrode 105 and the current supply electrode 102 must be in a proper range. If this distance is too large, the distributions and quantities of the nonfat part 109 and visceral fat 110 will affect the measured voltage V. If the distance is too small, the shapes and sizes of the electrodes and contact states between the electrodes and the subject 101 will affect the measured voltage V. The distance between the measuring electrode 105 and the current supply electrode 102 is preferably 0.5 to 3 times an average thickness of the subcutaneous fat 108. If the thickness of the subcutaneous fat 108 is 1 to 4 cm, the distance (center-to-center distance) between the current supply electrodes 102 and 103 is preferably 1 cm to 15 cm, more preferably, 2 cm to 10 cm. At this time, the distance (center-to-center distance) between the measuring electrode 105 and the current supply electrode 102 is preferably 0.6 cm to 10 cm, more preferably, 1 cm to 6 cm.

The distance between the electrodes 102 and 103 and the distance between the electrode 105 and the electrode 102 may be fixed for different subjects to measure. Alternatively, they may be changed in proportion to the circumferential length of each subject to measure. When changing the electrode-to-electrode distances in proportion to the circumferential length of a subject, the electrodes may be fixed to a belt made of elastic material such as rubber. When the belt is wound around the body of a subject, it expands according to the size of the body. Instead, the circumferential length of a subject is separately measured, and the electrode-to-electrode distances may mechanically be adjusted according to the measurement.

Figure 5A:
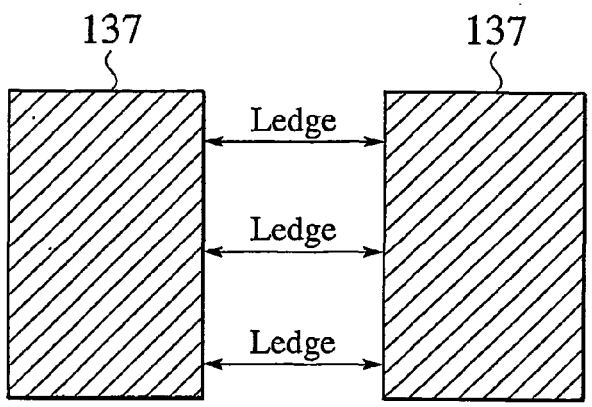
FIGS. 5A and 5B show edge distances between electrodes.
Figure 5B:
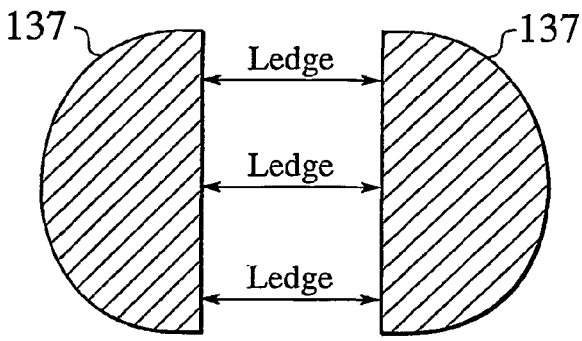

The shapes of the electrodes are, for example, disks or rectangles. It is preferable that the electrode shapes maintain an equal edge-to-edge distance $L_{edge}$ between the edges of adjacent electrodes like the rectangles of FIG. 5A and the semicircles of FIG. 5B. If disk electrodes are employed, they may have a diameter of 0.6 cm to 3.5 cm, preferably, 1.5 cm to 2.5 cm. If rectangular electrodes are employed, they may have a lateral length of 0.6 cm to 3 cm and a longitudinal length of 1.5 to 7 cm.

According to the first embodiment, the electrodes 102, 103, 105, and 111 of FIG. 1 may be changed to other positions on a circumferential surface of the subject 101 to measure another voltage through the measuring method of FIG. 1. According to a plurality of measured voltages and a characteristic quantity representing the size of the subject 101, the quantity of the visceral fat 110 of the subject 101 will be computed more precisely.

Figure 2A:
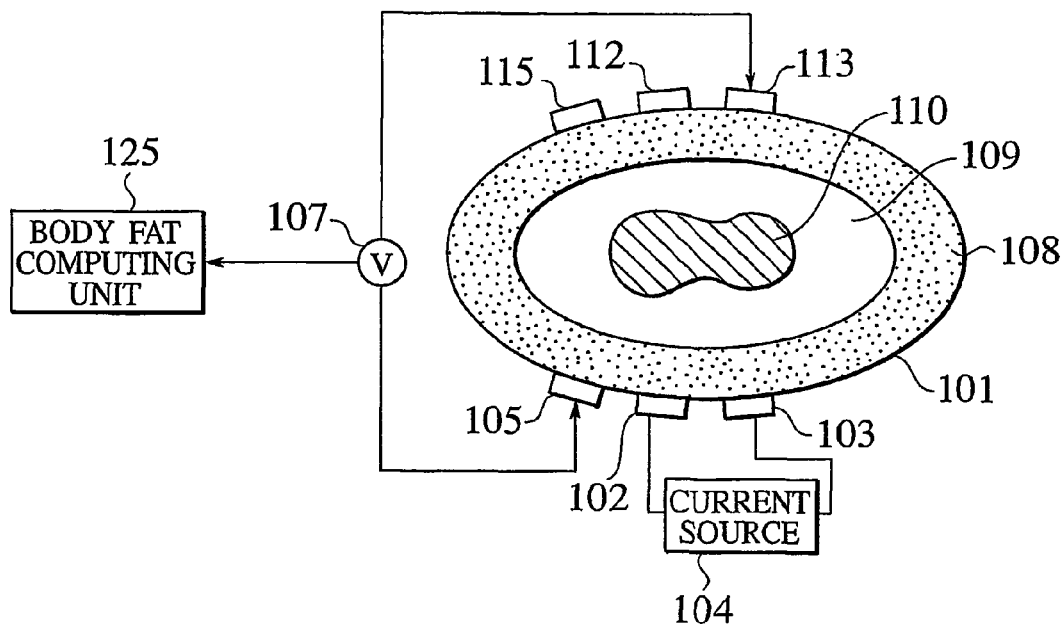
FIGS. 2A and 2B show a body fat measuring apparatus according to an alteration of the first embodiment.
Figure 2B:
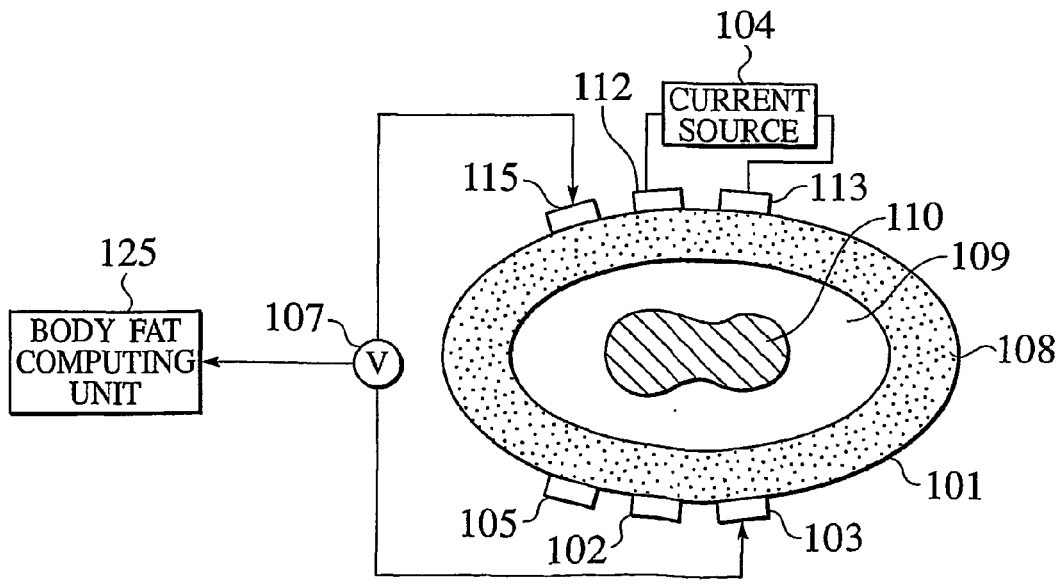

FIGS. 2A and 2B show an alteration of the first embodiment of FIG. 1. The alteration employs electrodes 112, 113, and 115 instead of the electrode 111 of FIG. 1.

In FIG. 2A, the current source 104 supplies a current between the electrodes 102 and 103, and the voltmeter 107 measures a voltage V generated between the electrodes 105 and 113. In FIG. 2B, the current source 104 supplies a current between the electrodes 112 and 113, and the voltmeter 107 measures a voltage V' generated between the electrodes 103 and 115. The body fat computing unit 125 computes a visceral fat quantity of a subject 101 according to the measured voltages V and V' and a characteristic quantity representing the size of the subject 101. At this time, the positions of the electrodes on the subject 101 are determined to most correctly measure the quantity of the visceral fat 110. For example, the electrodes 102, 103, and 105 are positioned on the back of the subject 101, and the electrodes 112, 113, and 115 are positioned in the vicinity of the navel of the subject 101. A correlation expression to calculate the quantity m of the visceral fat 110 according to the voltages V and V' measured by the voltmeter 107 and the characteristic quantity λ representing the size of the subject 101 may be as follows:

$$m = a0 + a1 \cdot \lambda^{\alpha} - (a2 \cdot V + a3 \cdot V') \cdot \lambda'^{\beta},$$

here a0, a1, a2, and a3 are regression coefficients, λ' is a characteristic quantity representing the size of the subject 101 and may be equal to λ, and α and β are exponents that are typically each 2 (α=β=2). The exponents α and β are not limited to 2 and are determined to provide an optimum correlation.

First Modification

Figure 3:
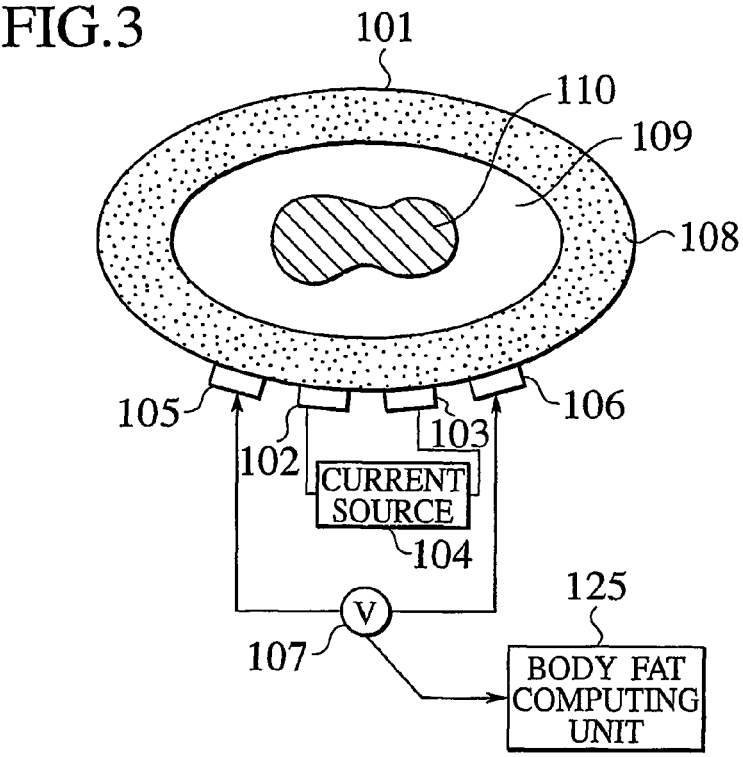
FIG. 3 shows a body fat measuring apparatus according to a first modification based on the first embodiment.

FIG. 3 shows a body fat measuring apparatus according to a first modification based on the first embodiment. The apparatus has two current supply electrodes 102 and 103 that are arranged on the surface of the body of a subject 101. The distance between the electrodes 102 and 103 is sufficiently shorter than a circumferential length of the subject 101. The apparatus also has a current source 104, measuring electrodes 105 and 106 arranged in the vicinities of the electrodes 102 and 103, a voltmeter 107 to measure a voltage generated between the electrodes 105 and 106, and a body fat computing unit 125 to compute a visceral fat quantity of the subject 101 according to the measured voltage and a characteristic quantity representing the size of the subject 101. The characteristics of the current source 104, the technique of preparing a correlation expression, the distance between the current supply electrodes, distances between the current supply electrodes and the measuring electrodes, the shapes of the electrodes, etc., of the first embodiment are applied to this modification.

A method of measuring a body fat quantity with the apparatus of FIG. 3 will be explained. The current source 104 supplies a current between the electrodes 102 and 103. The voltmeter 107 measures a voltage generated between the measuring electrodes 105 and 106. The computing unit 125 computes a visceral fat quantity of the subject 101 according to the measured voltage and a separately measured characteristic quantity representing the size of the subject 101. The voltage V measured with the voltmeter 107 corresponds to the quantity of the subcutaneous fat 108, and therefore, the quantity of the visceral fat 110 is calculable from a correlation expression prepared like the first embodiment. The positions of the electrodes 102, 103, 105, and 106 on the subject 101 are determined to most correctly find the quantity of the visceral fat 110. For example, they are positioned on the back of the subject 101 where the quantity of the subcutaneous fat 108 is large.

According to the first modification, the electrodes 102, 103, 105, and 106 of FIG. 3 may be changed to other positions on the circumferential surface of the subject 101 to measure another voltage with the measuring method of FIG. 3. According to a plurality of measured voltages and a characteristic quantity representing the size of the subject 101, the quantity of the visceral fat 110 of the subject 101 will be computed more accurately.

Second Modification

Figure 4:
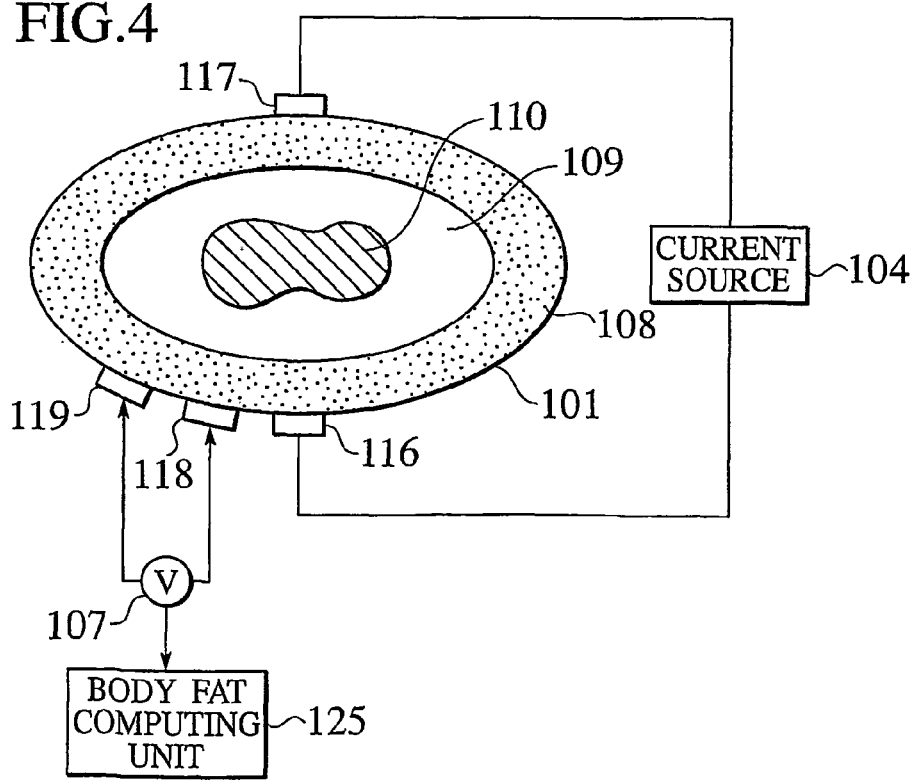
FIG. 4 shows a body fat measuring apparatus according to a second modification based on the first embodiment.

FIG. 4 shows a body fat measuring apparatus according to a second modification based on the first embodiment. The apparatus has two current supply electrodes 116 and 117 arranged substantially opposite to each other on the circumferential surface of a subject 101, a current source 104, two measuring electrodes 118 and 119 arranged on the circumferential surface of the subject 101 in the vicinity of the electrode 116 with the distance between the electrodes 118 and 119 being sufficiently smaller than the circumferential length of the subject 101, a voltmeter 107 to measure a voltage V generated between the electrodes 118 and 119, and a body fat computing unit 125 to compute the quantity of visceral fat 110 in the subject 101 according to the voltage measured by the voltmeter 107 and a characteristic quantity representing the size of the subject 101.

The current supply electrodes 116 and 117 may be arranged on the back and abdomen of the subject 101, respectively, or on the flanks of the subject 101, respectively. To more accurately compute a visceral fat quantity, it is preferable that the electrodes 116 and 117 are arranged on the back and abdomen of the subject 101, respectively.

A method of measuring a body fat quantity with the apparatus of FIG. 4 will be explained. The current source 104 supplies a current between the current supply electrodes 116 and 117. The voltmeter 107 measures a voltage generated between the measuring electrodes 118 and 119. The computing unit 125 computes a visceral fat quantity of the subject 101 according to the measured voltage and a separately measured characteristic quantity representing the size of the subject 101. The voltage V measured with the voltmeter 107 corresponds to the quantity of the subcutaneous fat 108, and therefore, the quantity of the visceral fat 110 is calculable from a correlation expression prepared like the first embodiment. The characteristics of the current source 104, the technique of preparing a correlation expression, the shapes of the electrodes, etc., of the first embodiment are applied to this modification.

The distance between the measuring electrodes 118 and 119 is preferably less than ⅙, more preferably, ⅛ of the circumferential length of the subject 101. If the distance between the electrodes 118 and 119 is too large, the measured voltage V is affected by the distribution and quantity of the visceral fat 110. If the distance between the electrodes 118 and 119 is too small, a potential difference generated between the electrodes 118 and 119 is insufficient for the measuring sensitivity of the voltmeter 107. Accordingly, the distance (center-to-center distance) between the electrodes 118 and 119 is preferably 3 cm or longer.

The distance between the current supply electrode 116 and the measuring electrode 118 must be in a proper range. If this distance is too large, the distributions and quantities of the nonfat part 109 and visceral fat 110 affect the measured voltage V. If the distance is too small, the shapes and sizes of the electrodes and contact states between the electrodes and the subject 101 affect the measured voltage V. The distance between the electrodes 116 and 118 is preferably 0.5 to 3 times an average thickness of the subcutaneous fat 108 of the subject 101.

According to the second modification, the current supply and measuring electrodes may be changed to other positions on the circumferential surface of the subject 101 to measure another voltage with the measuring method of FIG. 4. According to a plurality of measured voltages and a characteristic quantity representing the size of the subject 101, the quantity of the visceral fat 110 of the subject 101 is computed more accurately.

Figure 6:
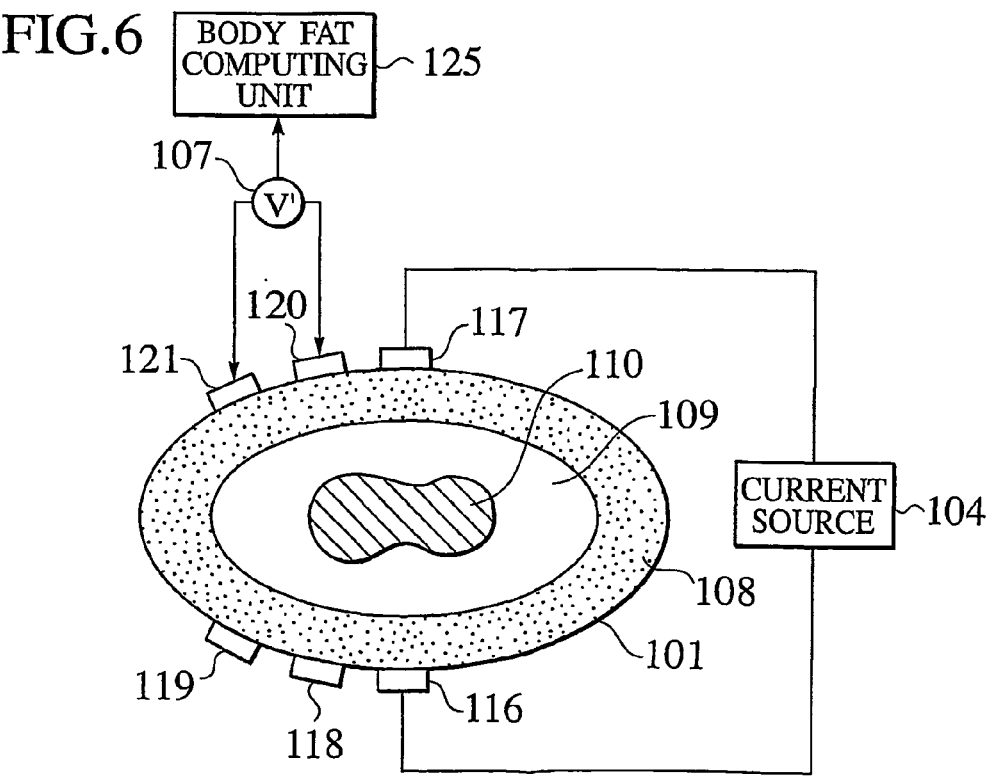
FIG. 6 shows a body fat measuring apparatus according to an alteration of the second modification.

FIG. 6 shows a body fat measuring apparatus according to an alteration of the second modification. The apparatus has a current source 104, current supply electrodes 116 and 117, two measuring electrodes 120 and 121 arranged in the vicinity of the electrode 117 with the distance between the electrodes 120 and 121 being sufficiently shorter than a circumferential length of a subject 101, a voltmeter 107 to measure a voltage V' generated between the electrodes 120 and 121, and a body fat computing unit 125. The computing unit 125 computes the quantity in of the visceral fat 110 of the subject 101 according to the voltage V measured with the voltmeter 107 of FIG. 4, the voltage V' measured with the voltmeter 107 of FIG. 6, and a separately measured characteristic quantity λ representing the size of the subject 101. A correlation expression used by the computing unit 125 may be as follows:

$$m = a0 + a1\cdot\lambda^\alpha - (a2\cdot V + a3\cdot V')\cdot\lambda'^\beta,$$

where a0, a1, a2, and a3 are regression coefficients, λ' is a characteristic quantity representing the size of the subject 101 and may be equal to λ, and α and β are exponents that are typically each 2 (α=β=2). The exponents α and β are not limited to 2 and are determined to provide an optimum correlation.

According to the present invention, contact resistance between a subject and electrodes is reduced by applying conductive gel or conductive gel sheets between the subject and the electrodes. The electric impedance of a subject (human) varies in a day. To correct a measurement error in a body fat quantity due to variations in a day in the electric impedance of a subject, a measured voltage may be corrected according to the time of measurement. The conditions of the abdomen of a subject changes before and after a meal. To correct a measurement error in a body fat quantity due to a meal, a measured voltage may be corrected according to an elapsed time between a meal and measurement.

A body fat quantity may be measured with currents of different frequencies. Measured results are compared with one another, to improve the reliability of body fat measurement.

SECOND EMBODIMENT

A body fat measuring apparatus according to the second embodiment of the present invention will be explained. This apparatus measures a visceral fat quantity such as a visceral fat sectional area in a human body.

Figure 7:
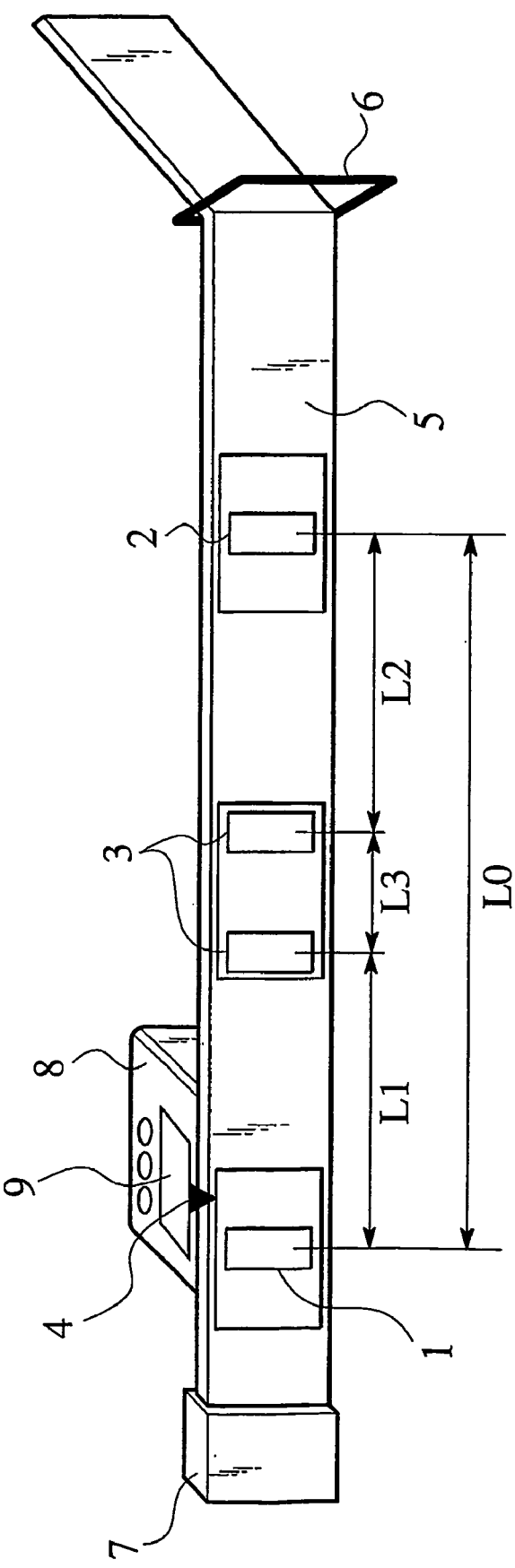
FIG. 7 shows a body fat measuring apparatus according to a second embodiment of the present invention.

FIG. 7 shows the body fat measuring apparatus according to the second embodiment. The apparatus has a first electrode group 1 including an electrode and arranged on the abdominal surface of a subject (human) with the navel of the subject serving as a reference position, a second electrode group 2 including an electrode and arranged on the back surface of the subject, a third electrode group 3 including two electrodes and arranged on the surface of the subject at an intermediate position between the first and second electrode groups, a navel marker 4 to indicate the reference position where the first electrode group 1 is positioned, a belt 5 that is substantially inelastic and then is not stretchable, buckles 6 and 7 to fix the belt 5 around the body of the subject, and a controller 8. Each of the first and second electrode groups 1 and 2 may include two or more electrodes. The third electrode group 3 may include thee or more electrodes. In this way, the body fat measuring belt according to the present invention includes the first electrode group 1, second electrode group 2, third electrode group 3, and navel marker 4.

The controller 8 has a measuring unit to supply a current between the electrode of the first electrode group 1 and the electrode of the second electrode group 2 and measure a voltage generated between the two electrodes of the third electrode group 3. The controller 8 also has a computing unit to compute an abdominal fat quantity of the subject around which the belt 5 is wound, according to the measured voltage. The controller 8 may have an input unit to enter physical data such as the circumferential length (waist measurement) U, sex, age (if required), etc., related to the subject, and a display 9 to display the entered data and calculated fat quantity. The computing unit computes an abdominal fat quantity of the subject according to the measured voltage and the entered data such as the waist measurement, sex, and age (if required) of the subject. The controller 8 is electrically connected to the first, second, and third electrode groups 1, 2, and 3 through electric cords. The cords may be embedded in the belt 5 so that they may not interfere with measuring operations.

Figure 8:
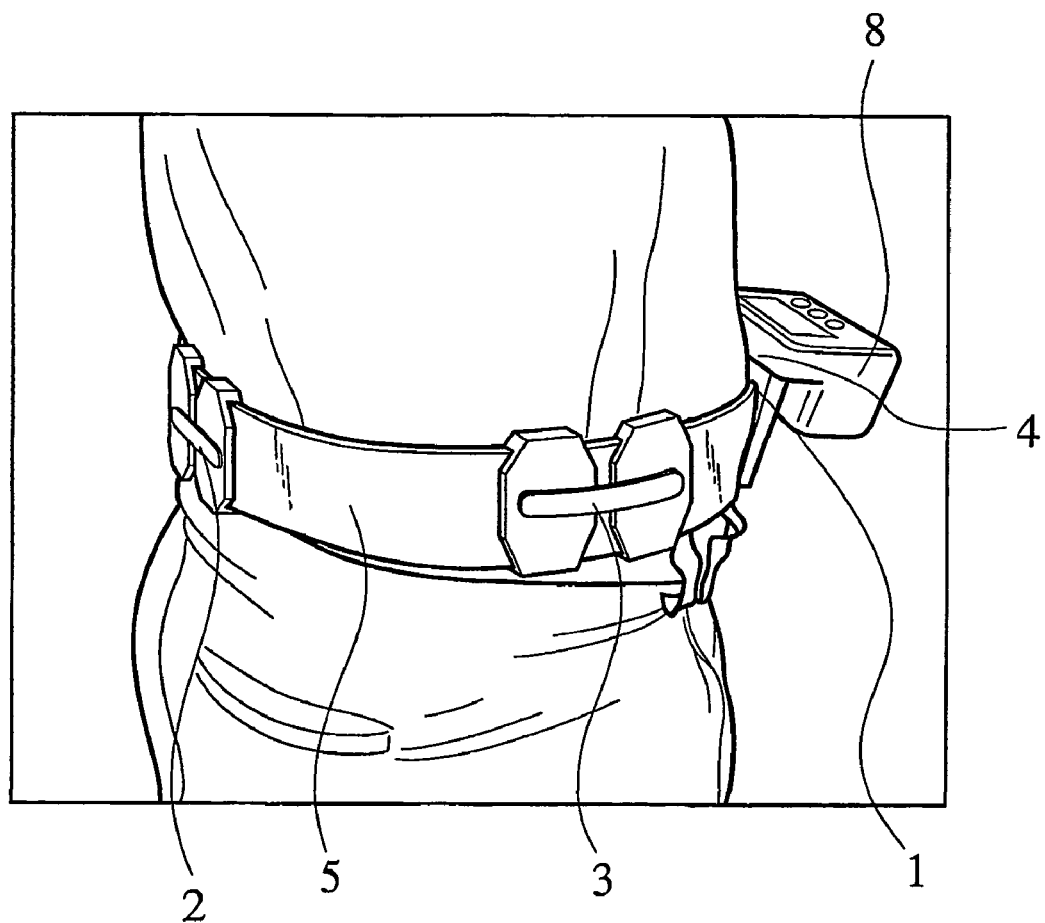
FIG. 8 shows the apparatus of FIG. 7 wound around the body of a subject.

A method of measuring a body fat quantity with the apparatus of FIG. 7 will be explained. As shown in FIG. 8, the belt 5 is wound around the waist of a subject so that the navel marker 4 is aligned with the navel of the subject. The belt 5 is tightened by adjusting the length thereof with the buckle 6, and the buckle 6 is joined with the buckler 7 to fix the belt 5 around the waist of the subject.

The controller 8 is manipulated to enter physical data such as the waist measurement U, sex, and age (if required) of the subject. When a start button on the controller 8 is pressed, the measuring unit of the controller 8 supplies a current between the electrode of the first electrode group 1 and the electrode of the second electrode group 2 and measures a voltage V generated between the two electrodes of the third electrode group 3. According to the measured voltage V and entered physical data, the computing unit of the controller 8 computes an abdominal fat quantity of the subject. The computed fat quantity is displayed on the display unit 9. The posture of the subject during the measurement may be standing, sitting, or lying. For the convenience and stability of the measurement, the standing posture is preferable. For cooperation with photographing an abdominal tomographic image with an X-ray CT system, the lying posture is preferable. A breathing state of the subject during the measurement may be natural expiration, natural inspiration, maximum expiration, maximum inspiration, etc. For the convenience and stability of the measurement, the natural expiration and inspiration are preferable. The measurement is usually carried out at a room temperature. For example, it is carried out at a temperature in the range of 0 to 40° C. For the convenience of the subject and good electric contact between the electrodes and the skin of the subject, a preferable temperature is in the range of 10 to 35° C.

The computed fat quantity is typically a visceral fat quantity in the abdomen of the subject, in particular, a visceral fat sectional area at a cross section of the body of the subject where the belt 5 is wound. Generally, a person having a large quantity of visceral fat has a large total fat quantity (the total of visceral and subcutaneous fat quantities). Accordingly, the apparatus of the present invention can approximate the total fat quantity of the subject.

The measuring unit of the controller 8 has a current source and a voltmeter. The current source is desirable to be an AC current source because it is easy to handle. The frequency of the AC current source may be in the range of 10 to 500 kHz, preferably, 50 to 200 kHz. A current value provided by the current source may be 0.3 to 3 mA. When the voltmeter measures a voltage (the amplitude or effective value of voltage), a phase delay may simultaneously be measured. The measured phase delay is used to analyze data.

A voltage V measured between the two electrodes of the third electrode group 3 represents a potential gradient appearing at an intermediate position between the first and second electrode groups 1 and 2 when a current is supplied between the electrode groups substantially across the body of a subject. This potential gradient strongly correlates with a visceral fat quantity. If the absolute value of the gradient is large, the visceral fat quantity is large, and if it is small, the visceral fat quantity is small. Moreover the potential gradient is substantially free from the influence of the distribution and quantity of subcutaneous fat, and therefore, is usable to easily and accurately calculate the quantity of visceral fat.

To compute the quantity of visceral fat, a correlation expression that relates a measured voltage V with a visceral fat quantity m is prepared in advance and is stored in the computing unit of the controller 8. To prepare such a correlation expression, a plurality of subjects having different values of fat quantity m are tested, and correlations between voltage V measured as mentioned above and visceral fat quantity m are found. When measuring the voltage V, the same current or different currents are applied to the subjects. When different currents are used, measured voltages must be standardized based on one current. To measure the visceral fat quantity m, tomographic images provided by an X-ray CT system or an MRI system are usable; based on the images, sectional areas and volumes serving as visceral fat quantities are calculated. When calculating a sectional area from a tomographic image, current spreading may be considered. That is, not only the tomographic image of one section but also the tomographic images of the vicinities may be prepared, and a visceral fat sectional area is calculated from an average of the tomographic images. This improves the correctness of the calculation. When computing a total fat quantity (the sum of visceral and subcutaneous fat quantities) from a measured voltage V, a correlation expression is prepared in the same manner.

The correlation expression may be prepared from a multivariate analysis and approximated with a linear polynomial. For example, the correlation expression is as follows:

$$m = a0 + a1 \cdot V \cdot U^n,$$

where m is a parameter representing a visceral fat quantity, a0 and a1 are regression coefficients, U is the waist measurement of a subject, and n is an exponent which may be null or a positive real number and is determined to provide an optimum correlation, and typically, n=1 to 3. The number of explanatory variables may be increased to improve the precision of the correlation expression. For example, the following expressions can be employed:

$$m = a0 + a1 \cdot V \cdot U^n + a2 \cdot U^{n'}, \text{ and}$$

$$m = a0 + a1 \cdot V \cdot U^n + a2 \cdot V \cdot U^{n'},$$

where a2 is a regression coefficient and n' is an exponent which is determined to provide an optimum correlation. The correlation expression may be prepared according to a nonlinear polynomial to improve computation accuracy or according to a function mapping V and U into m which is determined experimentally. Various types of nonlinear polynomials are employable. For example, the following is employable:

$$a0 \cdot m^3 + a1 \cdot m^2 + a2 \cdot m + a3 = V \cdot U^n,$$

where a0, a1, a2, and a3 are regressive coefficients. To improve computation accuracy, a different correlation expression may be used depending on the sex of a subject. That is, a correlation expression for male and a correlation expression for female are prepared, and one of them is chosen depending on information related to the sex of a subject entered into the input unit. Thereafter, a visceral fat quantity m of the subject is computed according to the correlation expression and a measured voltage V.

The belt 5 is made of a material that is substantially inelastic or not stretchable, such as vinyl, synthetic resin, synthetic leather, natural leather, woven fabric, and nonwoven fabric. The first to third electrode groups may directly be fixed to the belt 5, or may be arranged on a support that is flexible on the body of a subject. The support is fixed to the belt 5 and may be made of synthetic resin or rubber. The controller 8, first to third electrode groups, cords, etc., may be detachable from the belt 5, so that the belt 5 alone is washed or replaced with a new one. Scale marks may be added to the belt 5 to measure the waist of a subject. To maintain a constant tightening force by the belt 5 on the waist of a subject, the belt 5 may have scale marks so that the buckle 6 is set at a proper position on the belt 5 depending on the waist measurement of a subject. The belt 5 may employ elastic or stretchable material such as synthetic rubber or natural rubber at a part other than an intermediate part between the first and second electrode groups 1 and 2. To realize sufficient contact between the electrodes and the skin of a subject, the belt 5 may have an outer second belt, to provide a dual belt structure. Tightening the second belt strongly presses the electrodes on the belt 5 against the skin of a subject, to secure electrical contact between the electrodes and the skin.

When the apparatus of the second embodiment is placed around the body of a subject, the second electrode group 2 comes on the back of the subject and the third electrode group 3 on a flank of the subject. Since the first to third electrode groups are fixed on the inelastic belt 5, the positions of the second and third electrode groups 2 and 3 on the waist of the subject change depending on the waist measurement of the subject. To improve measuring accuracy, it is preferable to fix the electrodes on the belt 5 in such a way as to substantially equalize the distance L1 between the first and third electrode groups 1 and 3 with the distance L2 between the second and third electrode groups 2 and 3. Then, the third electrode group 3 detects a voltage generated at an intermediate point between the first and second electrode groups 1 and 2 irrespective of the waist measurement of the subject. When measuring subjects having waist measurements of 60 to 110 cm, the distance between the first and second electrodes 1 and 2 along the belt 5 is preferably 35 to 50 cm, in particular, 40 to 45 cm. The distance between the first electrode group 1 and the navel marker 4 is, for example, 1 cm to 6 cm.

The apparatus of the second embodiment may be constituted such that the third electrode group 3 comes on the light or left flank of a subject. If the third electrode group 3 is on the right flank of a subject, it is far from the stomach, and therefore, is less affected by eating.

The distance between the two electrodes of the third electrode group 3 is preferably set in an optimum range. If the distance is too short, a potential difference generated between the electrodes will be insufficient for the measuring sensitivity of the measuring unit in the controller 8. A preferable distance (center-to-center distance) between the electrodes is 3 cm or larger. If the distance is too large, a measured voltage will be affected by the distribution and quantity of subcutaneous fat. It is preferable, therefore, that the distance between the electrodes is shorter than ⅙ of the waist measurement of a subject. If the waist measurement is 60 to 110 cm, the electrode-to-electrode distance of the third electrode group 3 is preferably 3 to 10 cm.

The shapes of the electrodes are, for example, disks or rectangles as explained in the first embodiment. If disk electrodes are employed, they may have a diameter of 0.6 cm to 3.5 cm, preferably, 1.5 cm to 2.5 cm. If rectangular electrodes are employed, they may have a lateral length of 0.6 to 3 cm and a longitudinal length of 1.5 to 7 cm. The surface shapes of the electrodes may be flat, concave, or convex. If the surface of an electrode has a curvature radius that is too small, the electrode will not completely fit the skin of a subject, or a contact area between the electrode and the skin varies depending on an applied force, to destabilize electrical conditions. Accordingly, it is preferable that the electrodes have a curvature radius of 5 mm or greater. The electrodes may be made of a synthetic resin board plated with metal, a metal plate, or a conductive resin board. To reduce contact resistance, conductive liquid, conductive gel, conductive cream, or a conductive gel sheet may be applied between each electrode and the skin of a subject. The conductive liquid may be ion containing water such as tap water, cosmetic water, or saline water. To reduce contact resistance between the electrodes and the skin of a subject, it is preferable that the electrodes are placed on the skin for several seconds to several tens of seconds before an electrical measurement is started by pushing the start button on the controller 8.

Figure 9:
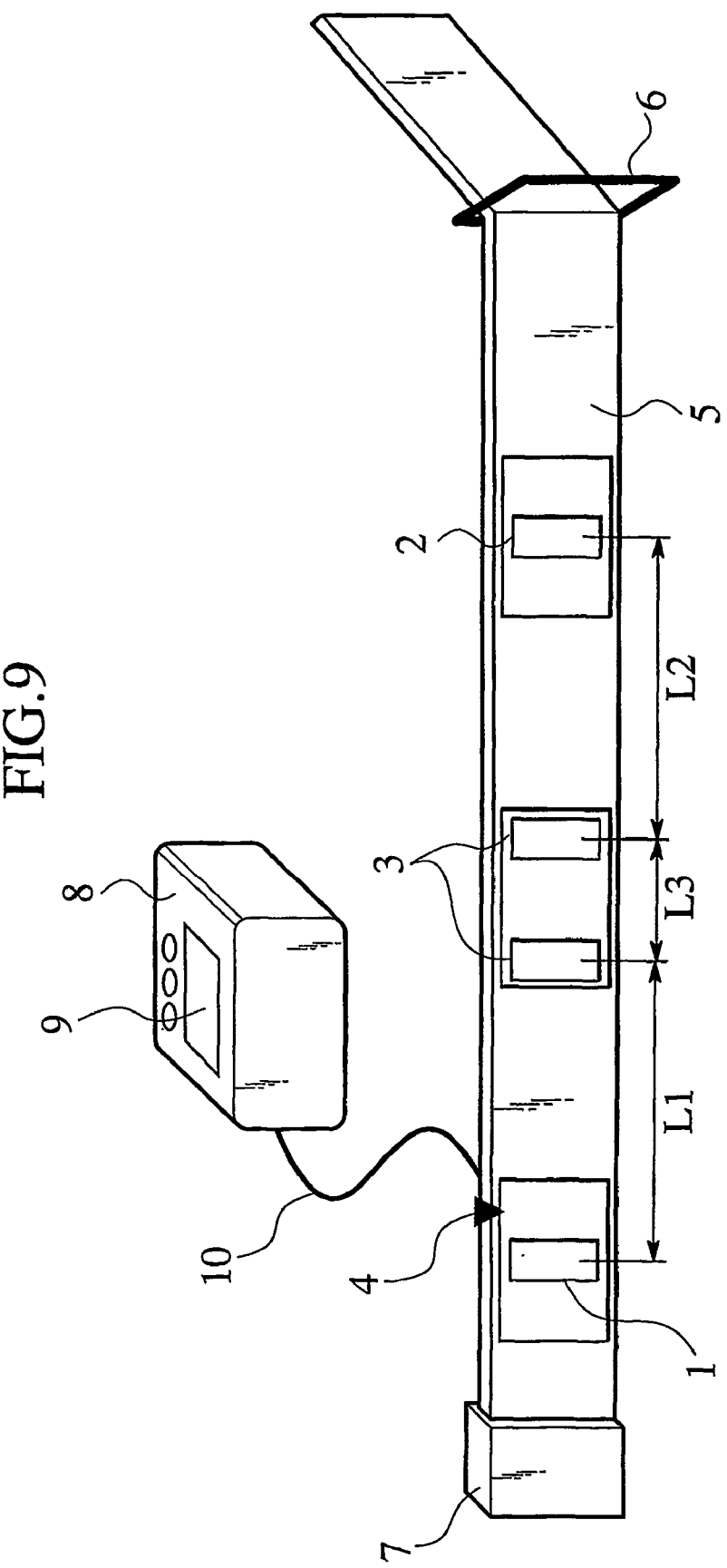
FIG. 9 shows a body fat measuring apparatus according to an alteration of the second embodiment.

FIG. 9 shows a body fat measuring apparatus according to an alteration of the second embodiment. The controller 8 is separated from the belt 5 and is connected thereto with a cord 10. The cord 10 may be detachable from the controller 8 or the belt 5. Connection between the controller 8 and the belt 5 may be realized through a wireless system using infrared rays or electromagnetic waves. In this case, the controller 8 and belt 5 are each provided with a transmit/receive circuit. The wireless system is applicable to the other embodiments, modifications, and alterations of the present invention.

As mentioned above, the controller 8 includes the voltage measuring unit (circuit) and computing unit (circuit). The controller 8 may also have a detachable storage unit such as a memory card to store computation results. The controller 8 may be connected to a wireless or wired control/communication unit such as a personal computer or a cellular phone to control voltage measuring, current supplying, and computing operations and transfer computation results.

Third Modification

Figure 10:
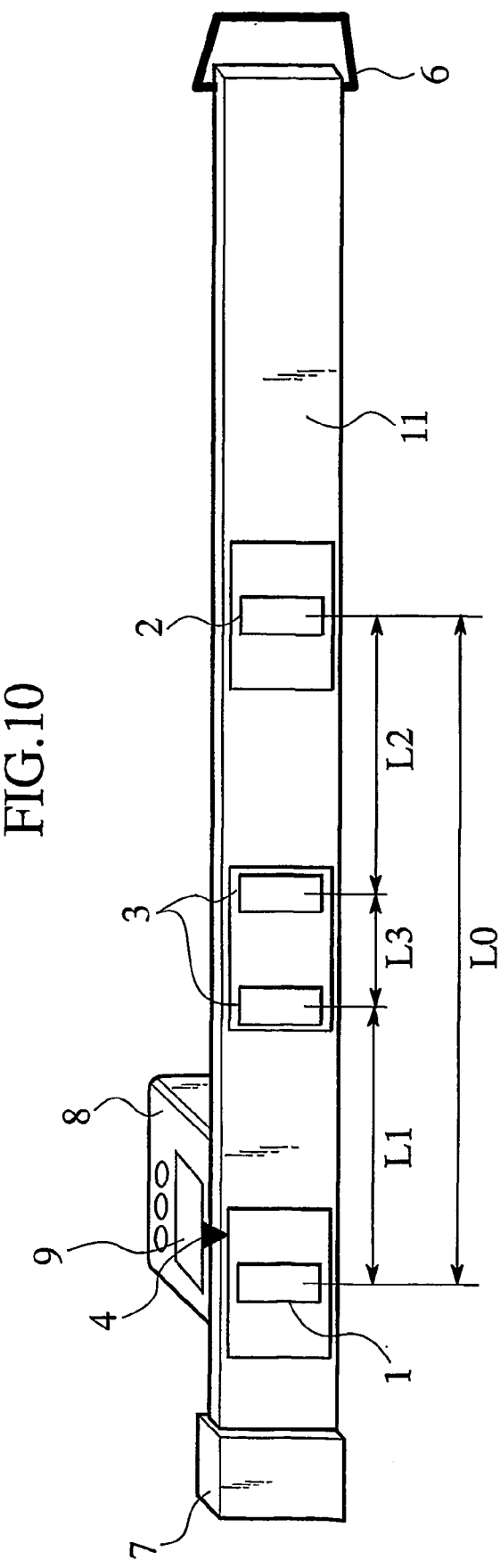
FIG. 10 shows a body fat measuring apparatus according to a third modification based on the second embodiment.

FIG. 10 shows a body fat measuring apparatus according to a third modification based on the second embodiment. This modification employs an elastic belt 11 instead of the inelastic belt 5 of the second embodiment and attaches a buckle 6 at an end of the belt 11. The other parts of the third modification are the same as those of the second embodiment. The elastic belt 11 may be made of elastic or stretchable material such as synthetic rubber, natural rubber, elastic unwoven fabric, or pleated synthetic resin. The belt 11 may entirely be made of elastic material, or may be a combination of elastic and inelastic materials. Measurement of a body fat quantity with the apparatus of FIG. 10 is made by expanding and winding the belt 11 around the waist of a subject and carrying out measurement operations like the second embodiment.

Since the belt 11 is made of elastic or stretchable material, distances between electrodes are adjustable and distances between electrode groups vary depending on the waist measurement of a subject. That is, the first to third electrode groups substantially maintain relative waist positions when applied to subjects having different waist measurements. A distance L0 between the first and second electrode groups is preferably ⅓ to ⅔ of an unextended length of the belt 11. It is preferable to arrange the electrode groups 1 to 3 on the belt 11 so that a distance L1 between the first and third electrode groups 1 and 3 is substantially equalized with a distance L2 between the second and third electrode groups 2 and 3. If a subject has a waist measurement of 60 to 90 cm, the unextended length of the belt 11 will be 56 to 59 cm. In this case, the distance between the first and second electrode groups 1 and 2 along the belt 11 may be 20 to 40 cm.

A relationship between a visceral fat quantity m and a measured voltage V is provided by a correlation expression like the second embodiment. A typical value of the exponent n in the correlation expression is n=1 to 3.

According to the third modification, the controller 8 may be separated from the belt 11 and connected thereto with a cord like the example of FIG. 9.

Fourth Modification

Figure 11:
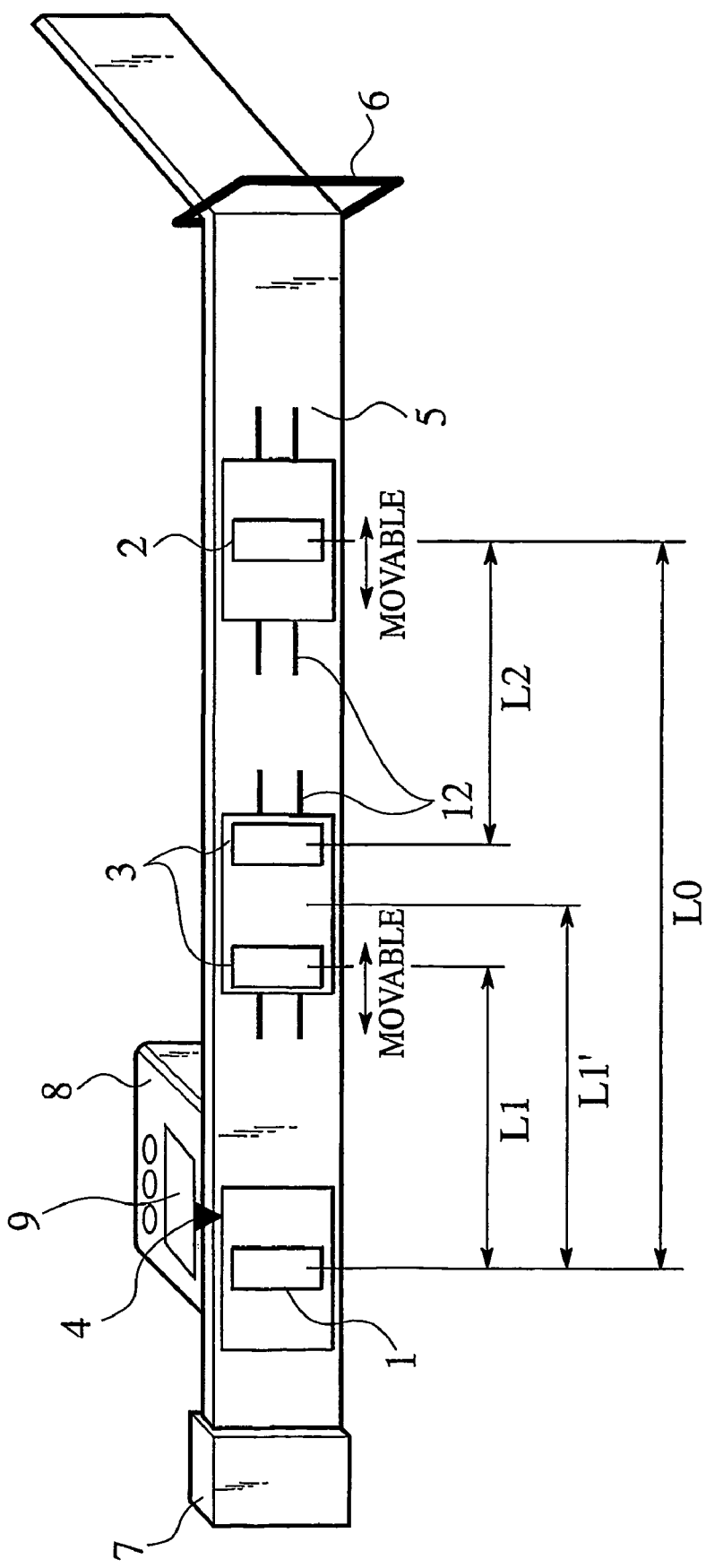
FIG. 11 shows a body fat measuring apparatus according to a fourth modification based on the second embodiment.

FIG. 11 shows a body fat measuring apparatus according to a fourth modification based on the second embodiment. An inelastic belt 5 has rails 12 at two locations, and a second electrode group 2 and a third electrode group 3 are arranged on the rails 12 so that the electrode groups may move on the rails 12. The other parts of the fourth modification are the same as those of the second embodiment. A method of measuring a body fat quantity with the apparatus of the fourth modification sets the second and third electrode groups 2 and 3 at optimum positions on a subject according to the waist measurement of the subject. The other operations are the same as those of the second embodiment.

According to the fourth modification, the second and third electrode groups 2 and 3 are movable on the rails 12. That is, distances between the electrode groups are adjustable along the belt 5 according to the waist measurement of a subject. A distance L0 between the first and second electrode groups 1 and 2 is preferably ⅓ to ⅔ of a waist measurement U of a subject. It is preferable to equalize a distance L1 between the first and third electrode groups 1 and 3 with a distance L2 between the second and third electrode groups 2 and 3. For example, the distance L0 between the first and second electrode groups is ½ of the waist measurement of a subject, and a distance L1' between the first electrode group 1 and a center position of the third electrode group 3 is ¼ of the waist measurement. These electrode group positioning rules are desirable to be applied to every subject. The rails 12 may have scale marks along them, so that the second and third electrode groups 2 and 3 may properly be positioned on the rails 12. According to the fourth modification, the controller 8 may be separated from the belt 5 and connected thereto with a cord like the example of FIG. 9.

Fifth Modification

Figure 12:
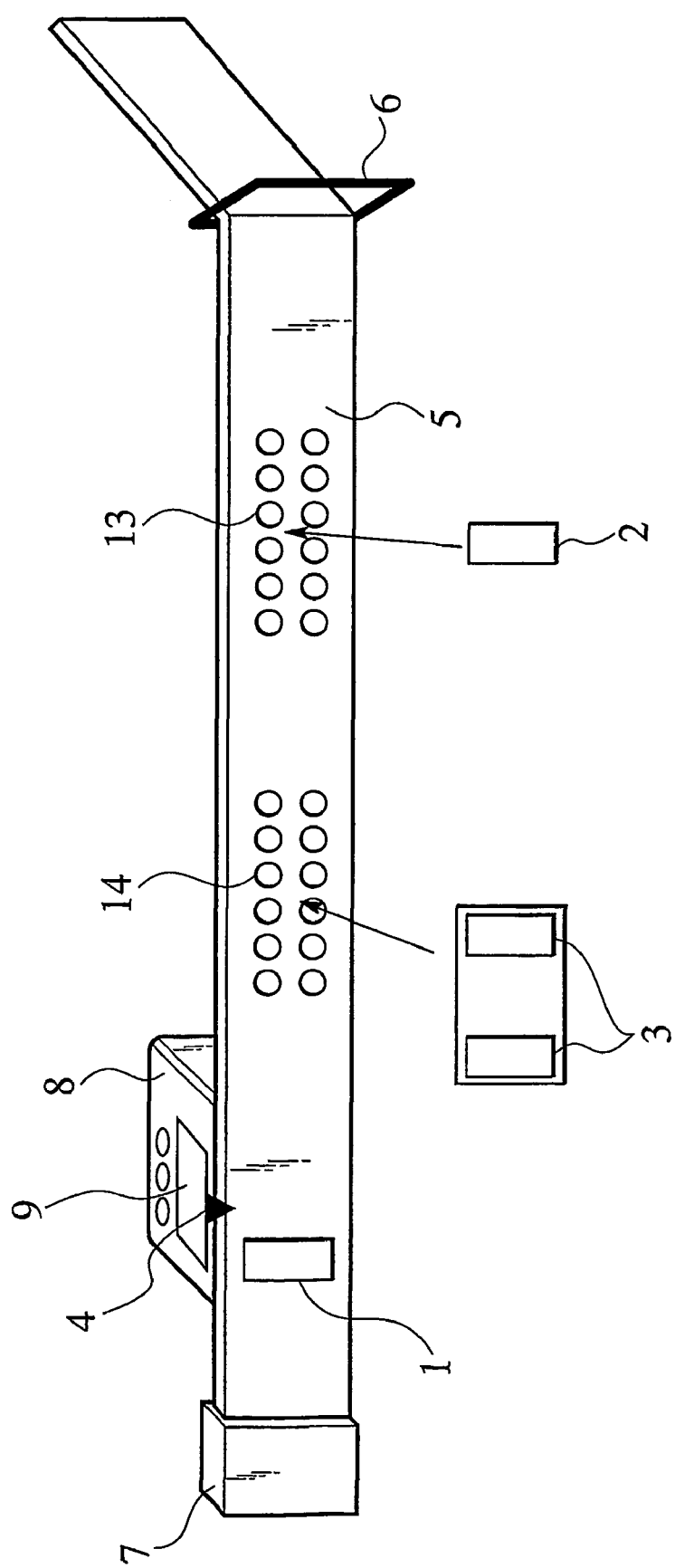
FIG. 12 shows a body fat measuring apparatus according to a fifth modification based on the second embodiment.

FIG. 12 shows a body fat measuring apparatus according to a fifth modification based on the second embodiment. The apparatus has a belt 5 having second electrode group receiving holes 13 and third electrode group receiving holes 14, so that second and third electrode groups 2 and 3 are attached to and detached from the belt 5. The other parts of the fifth modification are the same as those of the second embodiment. A body fat measuring method with the apparatus of the fifth modification will be explained. Proper ones of the holes 13 and 14 are chosen according to the waist measurement of a subject, and the second and third electrode groups 2 and 3 are set in the chosen holes. The other operations of the method are the same as those of the second embodiment. When the second and third electrode groups 2 and 3 are set in the holes 13 and 14, they are electrically connected to the controller 8 through electric wiring.

Choosing proper ones of the holes 13 and 14 and setting the second and third electrode groups 2 and 3 in the chosen holes enable to adjust distances between the electrode groups along the belt 5 according to the waist measurement of a subject. The distance between the first and second electrode groups 1 and 2 is preferably ⅓ to ⅔ of the waist measurement of a subject. It is preferable to equalize the distance between the first and third electrode groups 1 and 3 with the distance between the second and third electrode groups 2 and 3. For example, the distance between the first and second electrode groups 1 and 2 is ½ of the waist measurement of a subject, and the distance between the first electrode group 1 and a center position of the third electrode group 3 is ¼ of the waist measurement. These electrode group positioning rules are desirable to be applied to every subject. It is desirable to put scale marks along the holes 13 and 14, so that the second and third electrode groups 2 and 3 may properly be positioned according to the scale marks.

Sixth Modification

Figure 13:
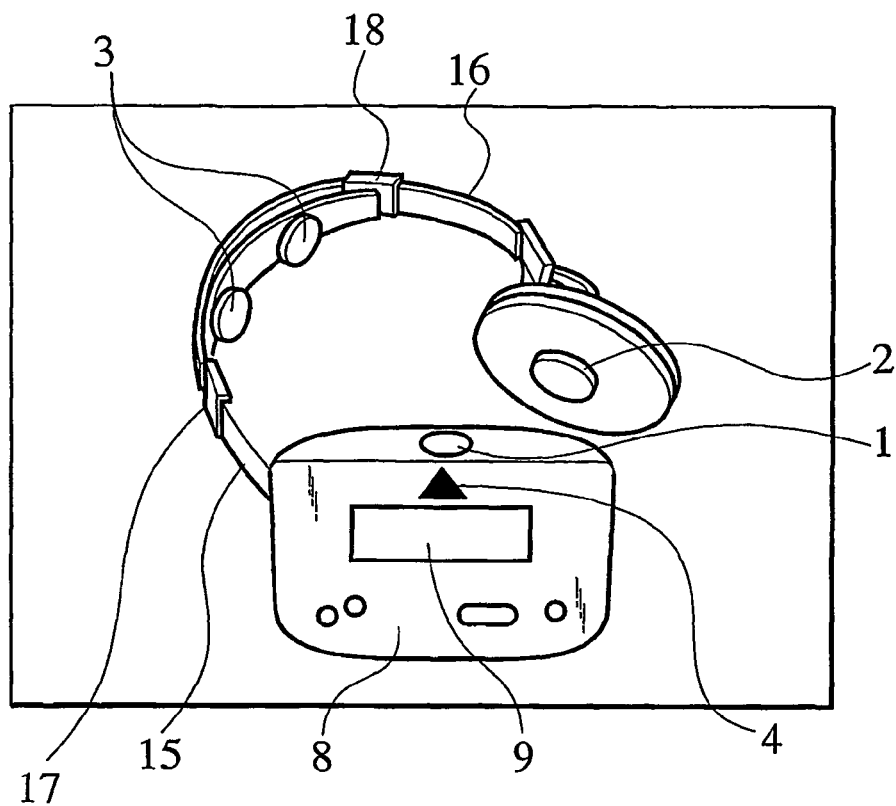
FIG. 13 shows a body fat measuring apparatus according to a sixth modification based on the second embodiment.

FIG. 13 shows a body fat measuring apparatus according to a sixth modification based on the second embodiment. The apparatus has a first electrode group 1 including an electrode and arranged on the abdominal surface of a subject with the navel of the subject serving as a reference position, a second electrode group 2 including an electrode and arranged on the back surface of the subject, a third electrode group 3 including two electrodes and arranged on the surface of the subject at an intermediate position between the first and second electrode groups, a navel marker 4 to indicate the reference position where the first electrode group 1 is positioned, an arm 15 to connect the first and third electrode groups 1 and 3 to each other, an arm 16 to connect the second and third electrode groups 2 and 3 to each other, a slider 17 to adjust the length of the arm 15, a slider 18 to adjust the length of the aim 16, and a controller 8. The controller 8 has a measuring unit to supply a current between the electrode of the first electrode group 1 and the electrode of the second electrode group 2 and measure a voltage generated between the two electrodes of the third electrode group 3, and a computing unit to compute an abdominal fat quantity of the subject according to the measured voltage.

The controller 8 may have an input unit to enter physical data such as the circumferential length (waist measurement), sex, age (if required), etc., of the subject, and a display 9 to display the entered data and calculated fat quantity. The computing unit computes the abdominal fat quantity of the subject according to the measured voltage and the data such as waist measurement, sex, and age (if required) of the subject. The controller 8 is electrically connected to the first, second, and third electrode groups 1, 2, and 3 through electric cords. The cords may be embedded in the arms 15 and 16 so that they may not interfere with measurement operations.

Figure 14:
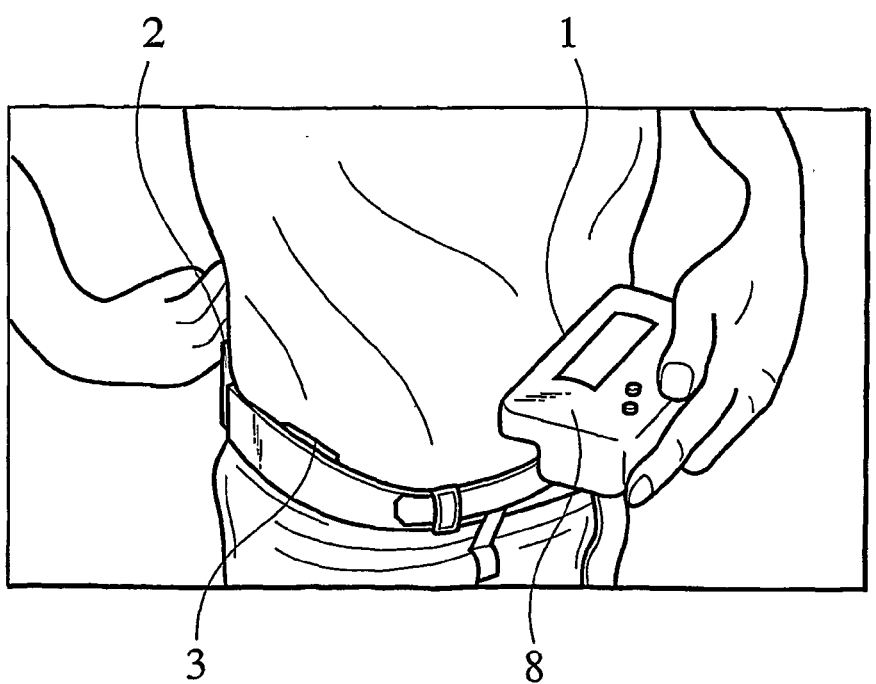
FIG. 14 shows the apparatus of FIG. 13 attached to the body of a subject.

A method of measuring a body fat quantity with the apparatus of the sixth modification will be explained. The controller 8 is manipulated to enter physical data such as the waist measurement, sex, and age (if required) of a subject. As shown in FIG. 14, the apparatus is attached to the waist of the subject from the right flank of the subject so that the first and second electrode groups 1 and 2 are on the abdomen and back of the subject, respectively. The sliders 17 and 18 are moved to adjust the lengths of the arms 15 and 16, and the third electrode group 3 is tightly attached to the flank of the subject. The navel marker 4 is aligned with the navel of the subject, and the first and second electrode groups 1 and 2 are pressed against the skin of the subject. And a start button on the controller 8 is pushed. Then, the measuring unit of the controller 8 supplies a current between the electrode of the first electrode group 1 and the electrode of the second electrode group 2 and measures a voltage generated between the two electrodes of the third electrode group 3. The computing unit of the controller 8 computes an abdominal fat quantity of the subject according to the measured voltage and entered physical data related to the subject. The computed fat quantity is displayed on the display 9.

The arms 15 and 16 are made of, for example, plastics (synthetic resin), rubber, wood, or ceramics and have each a C-shape. Adjusting the lengths of the arms 15 and 16 with the sliders 17 and 18 is carried out to equalize the distance between the first and third electrode groups 1 and 3 with the distance between the second and third electrode groups 2 and 3. The sliders 17 and 18 may have scale marks so that they may be adjusted according to the waist measurement of a subject. A support on which the second electrode group 2 is fixed may rotatably be connected to the arm 16, to make the orientation of the second electrode group 2 flexible and realize proper contact between the second electrode group 2 and the skin of a subject. Connection between the first electrode group 1 (controller 8) and the arm 15 may also be rotatable.

The computed fat quantity is typically a visceral fat quantity of the subject, in particular, a visceral fat sectional area at a cross section of the body of the subject where the first to third electrode groups are set. Generally, a person having a large quantity of visceral fat has a large total fat quantity (the total of visceral and subcutaneous fat quantities). Accordingly, the apparatus of the sixth modification can approximate the total fat quantity of the subject.

The sixth modification follows the second embodiment in regard to the posture and breathing of a subject during measurement, the characteristics of a current source and voltmeter, the preparation of a correlation expression, the position of the third electrode group 3, the distance between the two electrodes of the third electrode group 3, the shapes and materials of the electrodes, etc.

Seventh Modification

FIG. 15 shows a body fat measuring apparatus according to a seventh modification based on the second embodiment. The apparatus has a first electrode group 19 including two electrodes and arranged on the abdominal surface of a subject with the navel of the subject serving as a reference position, a second electrode group 20 including two electrodes and arranged on the back surface of the subject, a third electrode group 3 including two electrodes and arranged on the surface of the subject at an intermediate position between the first and second electrode groups 19 and 20, a navel marker 21 to indicate the reference position where the first electrode group 19 is positioned, a spine marker 22 to indicate a reference position where the second electrode group 20 is positioned, a controller 8, and cords 23 to electrically connect the controller 8 to the first to third electrode groups.

The controller 8 has a selector to select one of the two electrodes of the first electrode group 19 and one of the two electrodes of the second electrode group 20, a measuring unit to supply a current between the selected electrodes of the first and second electrode groups 19 and 20 and measure a voltage generated between the two electrodes of the third electrode group 3, and a computing unit to compute an abdominal fat quantity of the subject according to the measured voltage. The controller 8 may have an input unit to enter physical data such as the circumferential length (waist measurement), sex, age (if required), etc., of the subject, and a display 9 to display the entered data and computed fat quantity. The computing unit computes the abdominal fat quantity of the subject according to the measured voltage and the data such as waist measurement, sex, and age (if required) of the subject. The first to third electrode groups are attached to the surface of the subject with adhesive material or attachments such as suckers.

A method of measuring a body fat quantity with the apparatus of FIG. 15 will be explained. The navel marker 21 is aligned with the navel of a subject, and the first electrode group 19 is attached to the abdominal surface of the body 24 of the subject. The spine marker 22 is aligned with the spine of the subject, and the second electrode group 20 is attached to the back surface of the body 24. The third electrode group 3 is attached to the surface of the body 24 at an intermediate position between the first and second electrode groups 19 and 20. At this time, the height of the second and third electrode groups 20 and 3 is preferable to be equalized with the height of the first electrode group 19. For example, a laser pointer is used to emit a laser beam to the surface of the body 24 to conform the height where the electrode groups 3 and 20 are attached. The attaching height of the electrode groups is, for example, the height of the navel of the subject. An intermediate position between the first and second electrode groups 19 and 20 may be measured with a scale along the body 24, and the third electrode group 3 is attached to the measured intermediate position. The controller 8 is manipulated to enter physical data such as the waist measurement, sex, and age (if required) of the subject. A start button on the controller 8 is pushed, then the selector of the controller 8 selects one electrode from each of the first and second electrode groups 19 and 20. The measuring unit of the controller 8 supplies a current between the selected electrodes of the first and second electrode groups 19 and 20 and measures a voltage generated between the two electrodes of the third electrode group 3. The computing unit of the controller 8 computes an abdominal fat quantity of the subject according to the measured voltage and entered physical data and the computed fat quantity is displayed on the display 9.

The computed fat quantity is typically a visceral fat quantity of the subject, in particular, a visceral fat sectional area at a cross section of the body of the subject where the first to third electrodes are attached. Generally, a person having a large quantity of visceral fat tends to have a large total fat quantity (the total of visceral and subcutaneous fat quantities). Accordingly, the apparatus of the seventh modification can approximate the total fat quantity of the subject.

One may use the apparatus to measure the body fat quantity of a third person. In this case, the body 24 of FIG. 15 is of the third person whose body fat quantity is to be measured.

The electrode groups 3, 19, and 20 of the apparatus according to the seventh modification have attaching parts made of adhesive material or attachments such as suckers, so that the electrode groups may be attached to the surface of the body 24. Each of the attaching parts may have adhesive conductive gel, an adhesive conductive gel sheet, a sucker, or a structure employing adhesive tapes.

In FIG. 15, the two electrodes in each electrode group are together supported with a thin plastic plate 25 that curves along the surface of the body 24. The plastic plate 25 is not substantially stretchable, and therefore, the distance between the electrodes is kept at a constant value, and the flexibility of the plastic plate 25 makes the electrodes stably in contact with the surface of the body 24. The plastic plate 25 may be transparent to enable one to see the surface of the body 24 through the plastic plate 25. This makes it easier to carry out the positioning of the navel marker 21 and spine marker 22 when attaching the electrode groups to the body 24. The cords 23 may be detachable from the electrode groups 3, 19, and 20. When attaching the electrode groups to the surface of the body 24, the cords 23 are detached from the electrode groups, and after the electrode groups are attached to the body 24, the cords 23 are connected to the electrode groups. This prevents the cords 23 from interfering with the electrode groups when attached to the body 24 and makes it easier to attach the electrode groups to the body 24. To make the cords 23 detachable from the electrode groups, the cords 23 may be connected to the electrode groups with, for example, clips (mechanical connection) or magnets (magnetic connection).

The seventh modification follows the second embodiment in regard to the posture and breathing of a subject during measurement, the characteristics of a current source and voltmeter, the preparation of a correlation expression, the position of the third electrode group, the distance between the two electrodes of the third electrode group, the shapes and materials of the electrodes, etc.

In FIG. 15, the first and second electrode groups 19 and 20 include each a plurality of electrodes. Selecting each one electrode from the first and second electrode groups enables a current to flow in a different direction. A current may successively be passed in different directions, and voltages generated between the two electrodes of the third electrode group 3 may successively be measured, to correctly compute a visceral fat quantity according to the plurality of measured voltages. A correlation expression for the measured voltages V1, V2, . . . , and Vp and a visceral fat quantity m may be prepared according to a multivariate analysis as follows:

$$m = a0 + (a1 \cdot V1 + a2 \cdot V2 + \ldots + ap \cdot Vp) \cdot U^n$$
$$= a0 + U^n \sum_i ai \cdot Vi,$$

where a0, a1, . . . , and ap are regression coefficients, U is the waist measurement of the subject, and n is an exponent which may be null or a positive real number and is determined to provide an optimum correlation. If the quantity m is an absolute value such as a visceral fat sectional area, typically n=3. If the quantity m is a relative value such as the ratio of a visceral fat sectional area to the total sectional area of the body of the subject, typically n=1. To improve the accuracy of computation, a different correlation expression may be used depending on the sex of the subject.

Figure 16A:
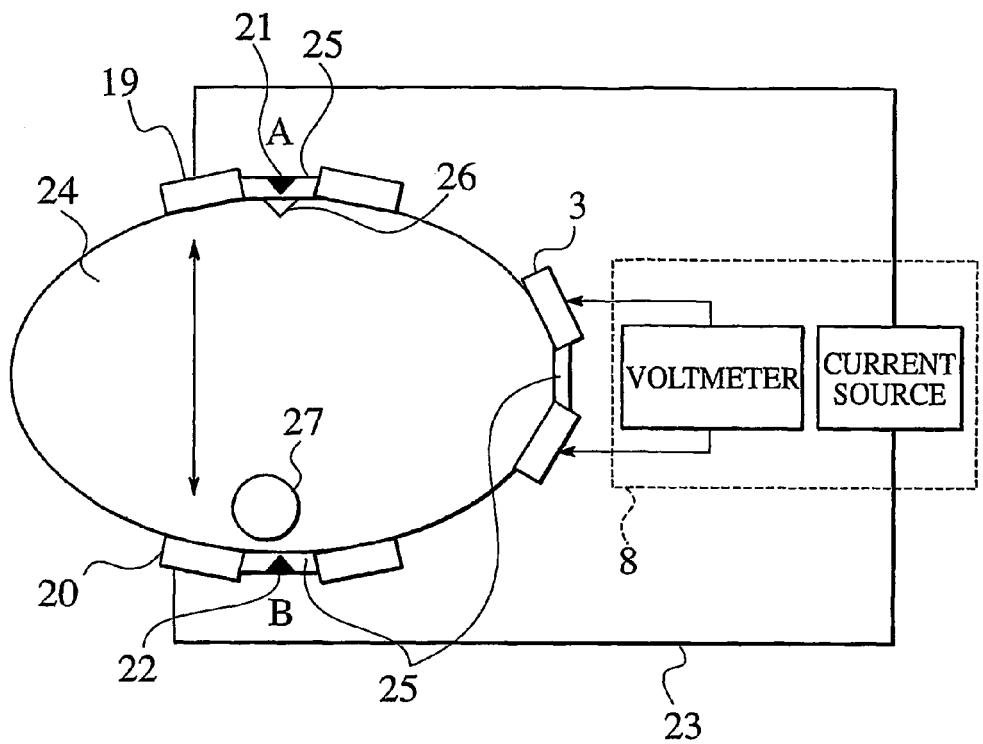
FIGS. 16A and 16B show examples of current paths formed by choosing different electrodes from the first and second electrode groups.
Figure 16B:
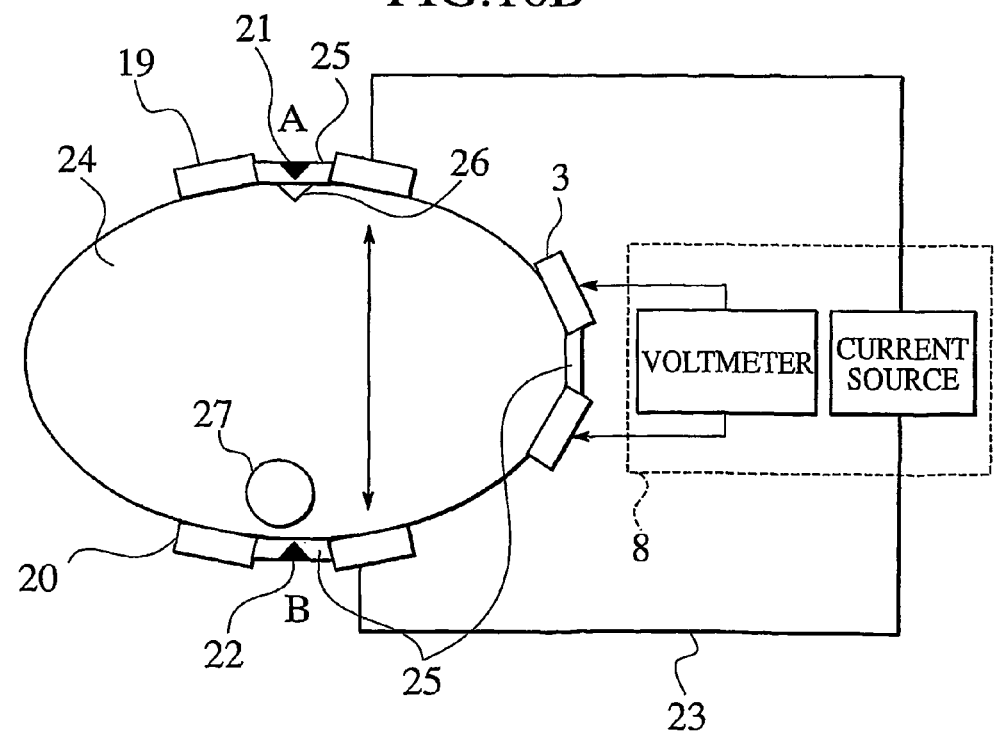

FIGS. 16A and 16B show examples of current paths formed by choosing different electrodes from the first and second electrode groups 19 and 20.

<Correlation Difference Between Male and Female>

Figure 26A:
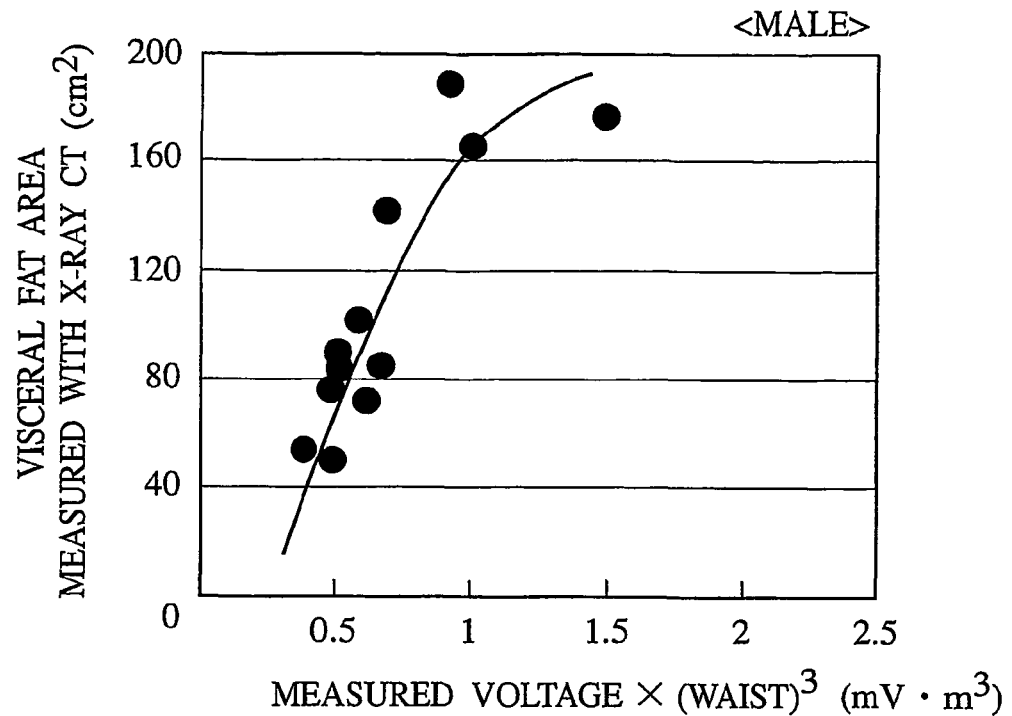
FIGS. 26A and 26B are graphs showing relationships between visceral fat quantities (areas) measured by an X-ray CT system and values measured by the apparatus of the seventh modification, these values being based on tests carried out by the inventor, the values of FIG. 26A relating to males and those of FIG. 26B to females.
Figure 26B:
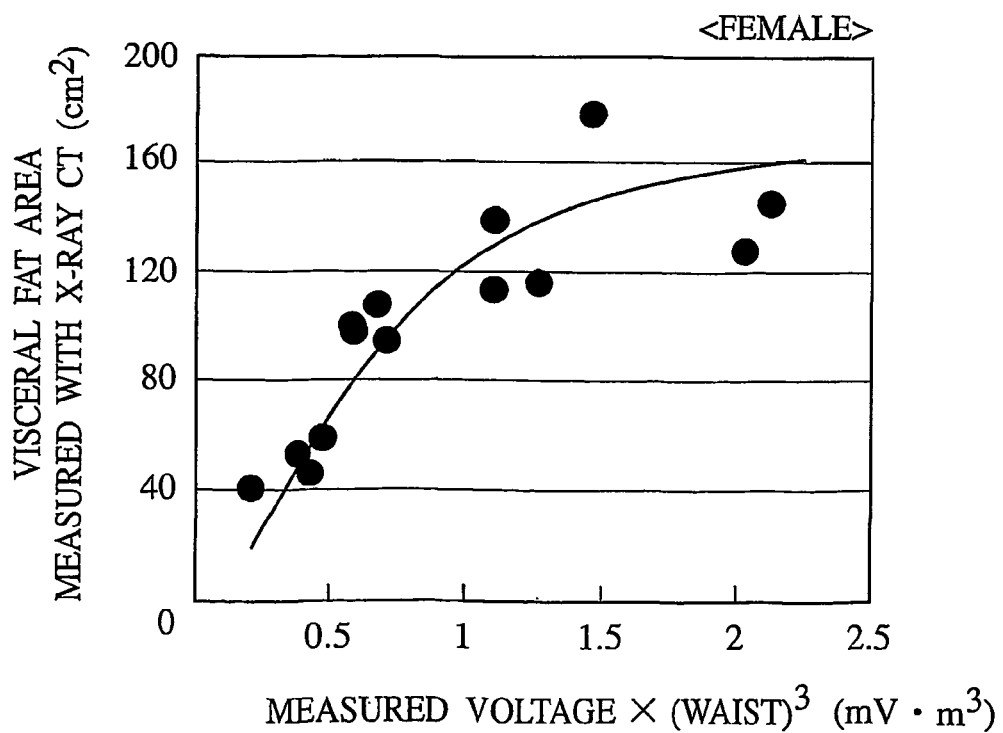

FIGS. 26A and 26B are graphs showing relationships between visceral fat quantities (areas) measured by an X-ray CT system and values measured by the apparatus of the seventh modification, in which the data of FIG. 26A are of males and those of FIG. 26B are of females. The data in FIGS. 26A and 26B are obtained by experiment carried out by the inventor. An abscissa represents measured voltage multiplied by (waist)³ and an ordinate represents visceral fat areas obtained from abdominal tomographic images taken by the X-ray CT system. Black dots represent the tested male and female subjects. The tests were made with the body fat measuring apparatus of FIG. 15 with an AC current of 1 mA at 100 kHz being passed through the current path of FIG. 16A. Voltages were measured at a room temperature.

As is apparent in FIGS. 26A and 26B, there are clear differences between males and females. When using the body fat measuring apparatus of the present invention, it is preferable to prepare correlation expressions for males and females separately, and employ one of them according to the sex of a subject entered through the input unit of the controller 8.

<Computation of Body Fat Quantity (Visceral Fat Quantity) in Consideration of Age>

Including the age Z of a subject in a correlation expression used by the body fat measuring apparatus of the present invention improves the accuracy of computation of a visceral fat quantity.

Figure 28:
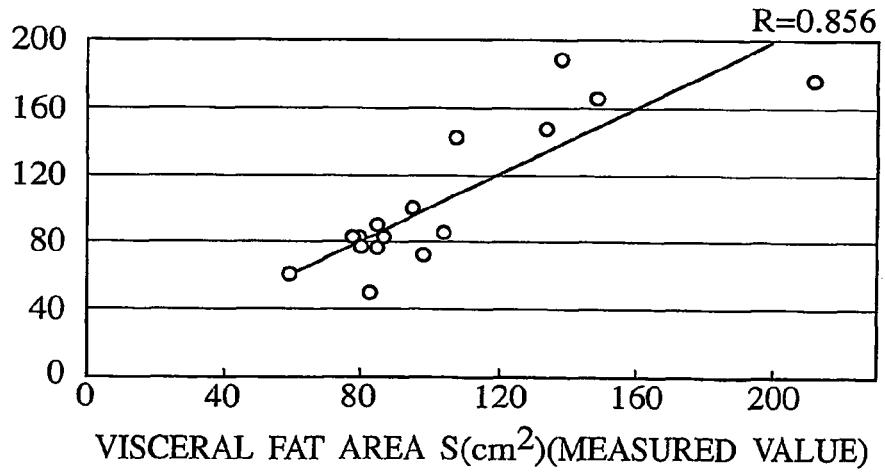
FIG. 28 is a graph showing relationships between visceral fat quantities (areas) measured by an X-ray CT system and visceral fat areas calculated with correlation expressions that consider no ages.

FIG. 28 is a graph showing relationships between visceral fat quantities (areas) S measured by an X-ray CT system and visceral fat areas calculated with correlation expressions without consideration of age. These relationships were obtained from tests carried out by the inventor. The tests were made with the body fat measuring apparatus of FIG. 15 with an AC current of 1 mA at 100 kHz being passed through the current path of FIG. 16A. Voltages were measured at a room temperature. The subjects tested were males. An abscissa represents visceral fat areas S calculated from the following correlation expression:

$$S = a0 + a1 \cdot V \cdot U^3,$$

where V is a measured voltage and U is the waist measurement of a subject. The tests show a multiple correlation coefficient of R=0.856.

Figure 29:
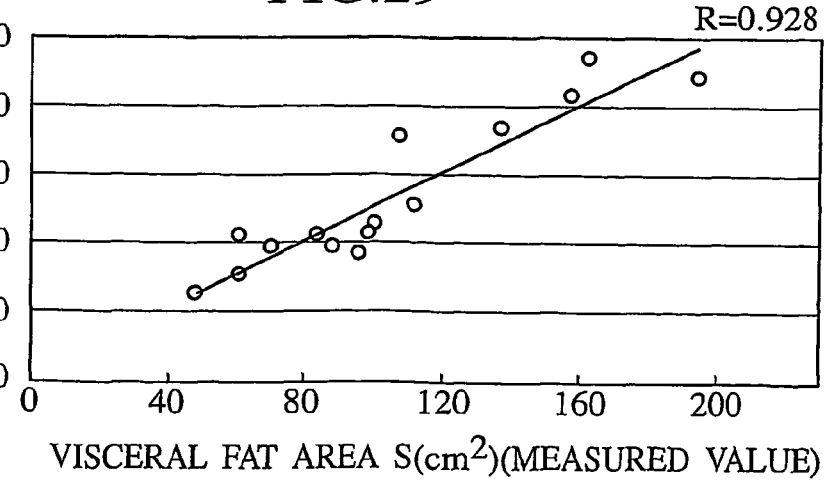
FIG. 29 is a graph showing relationships between visceral fat quantities (areas) measured by an X-ray CT system and visceral fat areas calculated with correlation expressions that consider ages.

FIG. 29 is a graph showing relationships between visceral fat quantities (areas) measured by an X-ray CT system and visceral fat areas calculated with correlation expressions in consideration of age. An abscissa represents visceral fat areas S calculated from the following correlation expression:

$$S = a0 + a1 \cdot V \cdot U^3 + b \cdot Z,$$

where V is a measured voltage, U is the waist measurement of a subject, Z is an age of the subject, and a0, a1, and b are regression coefficients. The tests show a multiple correlation coefficient of R=0.928.

Figure 27:
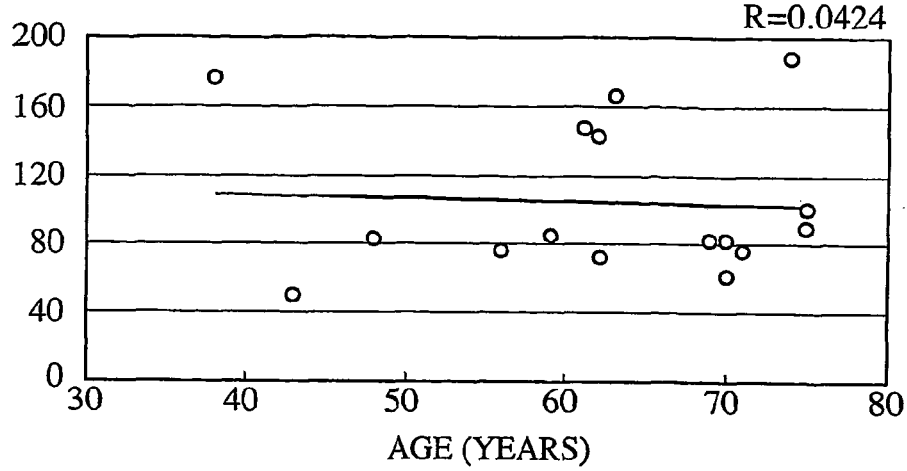
FIG. 27 is a graph showing relationships between ages and visceral fat quantities (areas) measured by an X-ray CT system.

As is apparent from the comparison of FIGS. 28 and 29, adding the age of a subject in a correlation expression like FIG. 29 realizes a multiple correlation coefficient close to "1" to indicate an improvement in the accuracy of computed visceral fat quantities. FIG. 27 is a graph showing relationships between ages and visceral fat quantities (areas) measured by an X-ray CT system and shows that the ages Z of subjects and the visceral fat areas thereof measured by the X-ray CT system have a weak correlation, i.e., a correlation coefficient of R=0.0424. It is therefore beyond expectation that combining the ages Z of subjects with measured voltages V and the waist measurements U of the subjects greatly improves a correlation between the visceral fat quantities measured by the X-ray CT system and the visceral fat quantities measured by the apparatus of the present invention. The improvement above probably comes from the fact that the correlation expressions involving the age of a subject properly correct the age dependence of the electric impedance of the subject when estimating a visceral fat area of the subject.

Any one of the second embodiment and the modifications 3 to 7 based on the second embodiment may enter the age Z of a subject in the input unit and include the age Z in explanatory variables to improve the accuracy of a correlation expression used to estimate a visceral fat quantity. The correlation expression may be as follows:

$$m = a0 + a1 \cdot V \cdot U^n + b \cdot Z,$$

$$m = a0 + a1 \cdot V \cdot U^n + a2 \cdot U^{n'} + b \cdot Z, \text{ or}$$

$$a0 \cdot m^3 + a1 \cdot m^2 + a2 \cdot m + a3 = V \cdot U^n + b \cdot Z,$$

where b is a regression coefficient. According to the seventh modification, the following expression can be also employed:

$$m = a0 + (a1 \cdot V1 + a2 \cdot V2 + \ldots + ap \cdot Vp) \cdot U^n + b \cdot Z$$

$$= a0 + U^n \sum_i ai \cdot Vi + b \cdot Z. \quad (i = 1, 2, \ldots, p)$$

According to the apparatus of FIG. 15, the first and second electrode groups 19 and 20 have each a plurality of electrodes. In this case, current supply electrodes and voltage measuring electrodes are properly selected to measure various voltages to compute a body fat quantity. For example, each one electrode is selected from the first and second electrode groups 19 and 20, to supply a current. The remaining electrodes of the first and second electrode groups 19 and 20 are used to measure a voltage V' generated between them, to find a total fat quantity m' at a corresponding abdominal section. The total fat quantity is, for example, the sum of a subcutaneous fat sectional area and a visceral fat sectional area. A correlation expression involving the voltage V' and total fat quantity m' may be prepared according to a multivariate analysis as follows:

$$m' = a0 + a1 \cdot V' \cdot U^n, \text{ or}$$

$$m' = a0 + a1 \cdot V' \cdot U^n + b \cdot Z,$$

where a0, a1, and b are regressive coefficients, U is the waist measurement of the subject, and n is an exponent which may be null or a positive real number and is determined to provide an optimum correlation.

ThIRD EMBODIMENT

Figure 17:
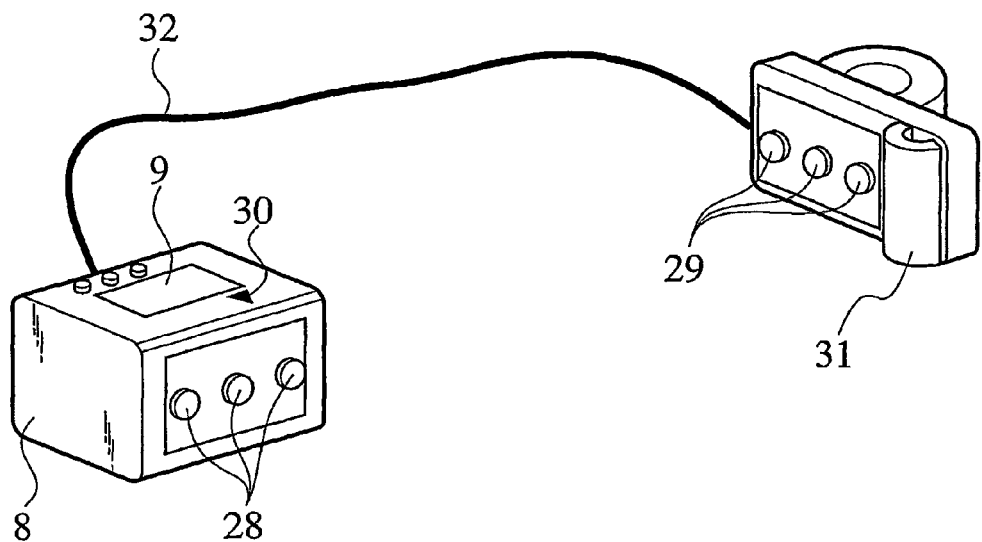
FIG. 17 shows a body fat measuring apparatus according to a third embodiment of the present invention.

FIG. 17 shows a body fat measuring apparatus according to the third embodiment of the present invention. This apparatus measures a subcutaneous fat quantity, which may be the thickness or sectional area of a subcutaneous fat layer of a subject (human), and a visceral fat quantity, which may be a visceral fat sectional area in the subject.

The apparatus of the third embodiment has a first electrode group 28 including three electrodes and arranged on the abdominal surface of a subject with the navel of the subject serving as a reference position, a second electrode group 29 including three electrodes and arranged on the back surface of the subject, a navel marker 30 to indicate the reference position where the first electrode group 28 is positioned, a spine marker 31 to indicate a reference position where the second electrode group 29 is positioned, a cord 32 to connect the first and second electrode groups 28 and 29 to each other, and a controller 8. The controller 8 has a measuring unit to supply a current between two electrodes selected from the second electrode group 29 and measure a voltage generated between an electrode selected from the first electrode group 28 and an electrode selected from the second electrode group 29. The controller 8 also has a computing unit to compute a body fat quantity of the abdominal part of the subject according to the measured voltage. The controller 8 may have an input unit to enter physical data such as the circumferential length (waist measurement), sex, age (if required), etc., of the subject, and a display 9 to display the entered data and computed fat quantity.

The computing unit computes the abdominal fat quantity of the subject according to the measured voltage and the data such as the waist measurement, sex, and age (if required) of the subject. The controller 8 is electrically connected to the first and second electrode groups 28 and 29 with cords. The cords to connect the controller 8 to the second electrode group 29 may be embedded in the cord 32. The cord 32 may be a C-shaped arm made of plastics (synthetic resin), rubber, wood, or ceramics.

Figure 18:
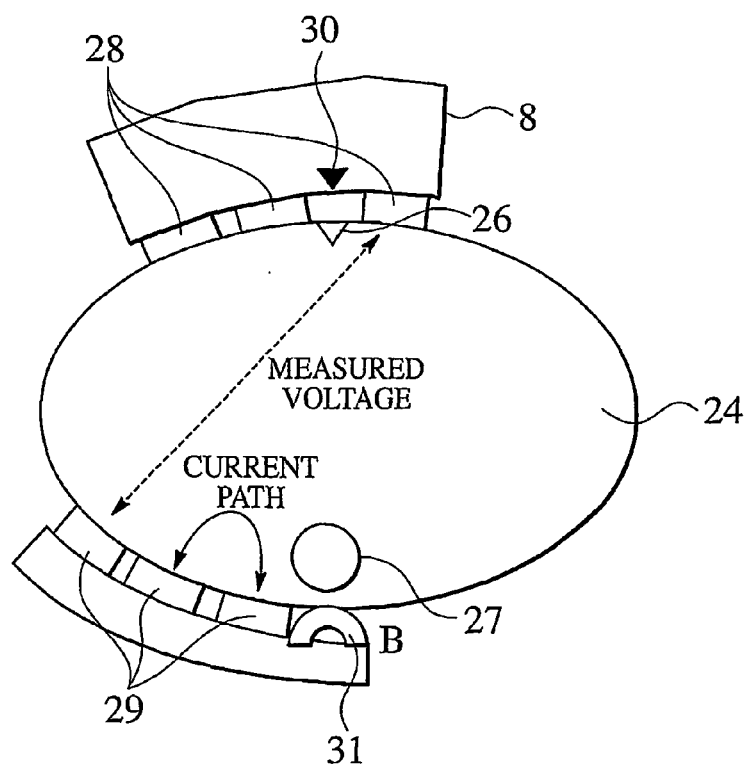
FIGS. 18 to 20 show examples of current paths formed to measure voltages according to the third embodiment.

A method of measuring a body fat quantity with the apparatus of the third embodiment will be explained. The controller 8 is manipulated to enter physical data such as the waist measurement, sex, and age (if required) of a subject whose body fat quantity is to be measured. The navel marker 30 is aligned with the navel of the subject and the first electrode group 28 is pressed against the surface of the abdominal part of the subject with one hand. With the other hand, the spine marker 31 is aligned with the spine of the subject and the second electrode group 29 is pressed against the back of the subject. These states are maintained, and a start button on the controller 8 is pushed. Then, the measuring unit of the controller 8 supplies a current between two electrodes selected from the second electrode group 29 and measures a voltage V1 generated between an electrode selected from the first electrode group 28 and an electrode selected from the second electrode group 29. The computing unit of the controller 8 computes an abdominal fat quantity of the subject according to the measured voltage V1 and entered physical data. The computed fat quantity is displayed on the display 9. The navel marker 30 and spine marker 31 serve to indicate the positions on the body surface of the subject where the electrode groups 28 and 29 are positioned. This enables the electrodes to stably maintain relative positions on any subject having any waist measurement. FIG. 18 shows an example of a current path formed by the apparatus of the third embodiment when measuring a voltage V1.

The body fat measuring apparatus according to the third embodiment is capable of measuring a subcutaneous fat quantity, which may be the thickness or sectional area of subcutaneous fat at a cross section of the body of a subject where the first and second electrode groups 28 and 29 are arranged, as well as a visceral fat quantity, which may be a visceral fat sectional area at the same cross section.

Two current supply electrodes are selected from the second electrode group 29 arranged on the back of a subject, and therefore, they pass a current around subcutaneous fat on the back of the subject. Accordingly, a measured voltage V1 corresponds to the thickness of the subcutaneous fat on the back of the subject. From the voltage V1, an average subcutaneous fat thickness d on the back where the second electrode group 29 is arranged is computable. Also from the voltage V1, a subcutaneous fat sectional area S on a cross section of the body of the subject can be approximated.

To compute the subcutaneous fat thickness d and sectional area S of a given subject, a correlation expression relating such quantities to a measured voltage must be prepared and stored in the computing unit of the controller 8. To prepare such a correlation expression, a plurality of subjects having different subcutaneous fat quantities are measured for voltages of V1 in such a manner mentioned above. When measuring voltages on the subjects, the same current or different currents may be applied to the subjects. When different currents are applied to the subjects, the measured voltages must be standardized based on one current. To measure the thickness d and sectional area S of subcutaneous fat of the subjects, an X-ray CT system or an MRI system is employed to provide tomographic images of the subjects, and based on the tomographic images, the subcutaneous fat thicknesses and sectional areas are obtained.

The correlation expression mentioned above may be prepared from a multivariate analysis and approximated with a linear polynomial. For example, the correlation expression to provide a subcutaneous fat thickness d is as follows:

$$d = a0 + a1 \cdot V1 \cdot U^n,$$

where a0 and a1 are regression coefficients, U is the waist measurement of a subject, and n is an exponent which may be null or a positive real number and is determined to provide an optimum correlation and is typically 1. Similarly, the correlation expression to provide a subcutaneous fat sectional area S is as follows:

$$S = a0 + a1 \cdot V1 \cdot U^n$$

If S is the absolute value of a subcutaneous fat sectional area, n is typically 2. If S is the ratio of a subcutaneous fat sectional area to a total sectional area, n is typically null. The number of explanatory variables may be increased to improve the precision of the correlation expressions. For example, the following can be employed:

$$d = a0 + a1 \cdot V1 \cdot U^n + a2 \cdot U^{n'}, \text{ and}$$

$$S = a0 + a1 \cdot V1 \cdot U^n + a2 \cdot U^{n'},$$

where a2 is a regression coefficient and n' is an exponent which is null or a positive real number and is determined to provide an optimum correlation. The correlation expressions may be prepared according to nonlinear polynomials to improve computation accuracy.

The age Z of a subject may be entered in the input unit of the controller 8, so that the age Z is included in explanatory variables, to improve the accuracy of the correlation expressions, as follows:

$$d = a0 + a1 \cdot V1 \cdot U^n + b \cdot Z, \text{ or}$$

$$d = a0 + a1 \cdot V1 \cdot U^n + a2 \cdot U^{n'} + b \cdot Z$$

$$S = a0 + a1 \cdot V1 \cdot U^n + b \cdot Z, \text{ or}$$

$$S = a0 + a1 \cdot V1 \cdot U^n + a2 \cdot U^{n'} + b \cdot Z,$$

where b is a regression coefficient.

To further improve computation accuracy, a different correlation expression may be used depending on the sex of a subject. That is, correlation expressions are prepared for males and females separately and a correlation expression used for fat computation is chosen according to the sex of a subject entered in the input unit. According to the chosen correlation expression and measured voltage V1, the thickness d or sectional area S of subcutaneous fat of the subject is computed.

Figure 19:
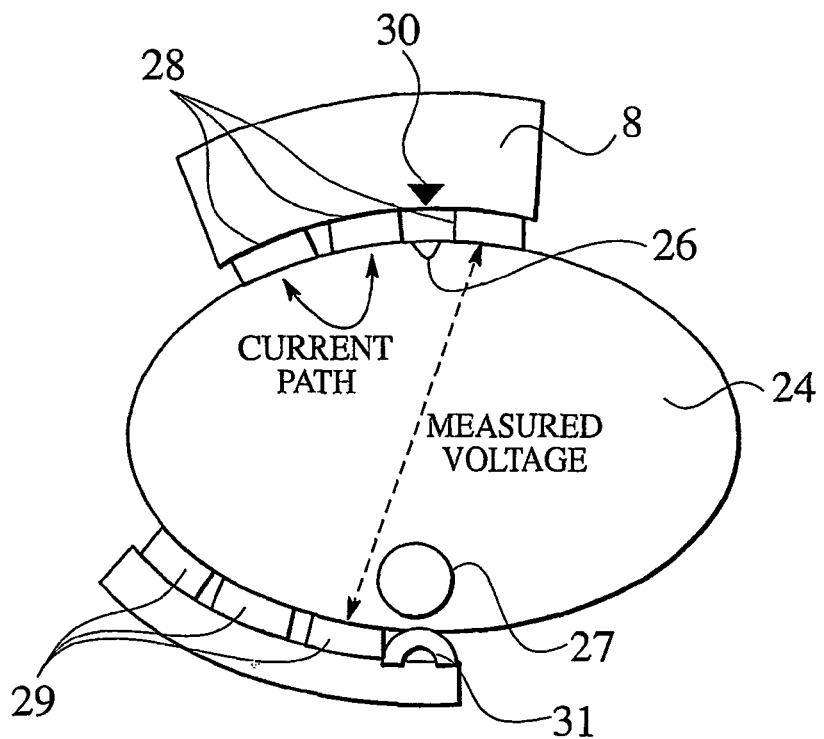

The body fat measuring apparatus of FIG. 17 has three or more electrodes in the first electrode group 28. Thus, in addition to measuring the voltage V1, the measuring unit of the controller 8 may supply a current between two electrodes selected from the first electrode group 28 and measure a voltage V2 generated between an electrode selected from the first electrode group 28 and an electrode selected from the second electrode group 29, to improve the computation accuracy of a subcutaneous fat sectional area S. In this case, the computing unit of the controller 8 may store the following correlation expression:

$$S=a0+(a1 \cdot V1+a2 \cdot V2) \cdot U^n,$$

where a2 is an additional regressive coefficient. This correlation expression may include an age term of "+b·Z" FIG. 19 shows an example of a current path to measure the voltage V2.

According to the measured voltage V1 and entered waist measurement U, the third embodiment is capable of measuring a visceral fat quantity such as a visceral fat sectional area at a cross section of the body of the subject where the first and second electrode groups 28 and 29 are arranged. The voltage V1 corresponds to a subcutaneous fat quantity, and the waist measurement corresponds to a total fat quantity (the sum of visceral and subcutaneous fat quantities). Therefore, a difference between them corresponds to the visceral fat quantity.

To compute the visceral fat quantity, a correlation expression that relates the voltage V1 and waist measurement U to the visceral fat quantity m is prepared in advance and stored in the computing unit of the controller 8. To prepare the correlation, the technique of the second embodiment is employed. The correlation expression may be prepared from a multivariate analysis and approximated with a linear polynomial. For example, the correlation expression is given by $$m=a0+a1 U^{n'}-a2 \cdot V1 \cdot U^n,$$

where a0, a1, and a2 are regression coefficients, U is the waist measurement of a subject, and n and n' are exponents which may be null or positive real numbers and are determined to provide an optimum correlation. If the quantity m represents the absolute value of a visceral fat sectional area, typically n'=1 to 2 and n=2. The correlation expression may be prepared in the form of a nonlinear polynomial to improve computation accuracy.

The age Z of the subject may be entered in the input unit of the controller 8, so that the age Z is included in explanatory variables, to improve the accuracy of the correlation expression, as follows:

$$m=a0+a1 \cdot U^{n'}-a2 \cdot V1 \cdot U^n+b \cdot Z,$$

where b is a regression coefficient. To further improve computation accuracy, a different correlation expression may be used depending on the sex of a subject. That is, correlation expressions are prepared for males and females separately and a correlation expression used for fat computation of a subject is chosen according to the sex of the subject entered in the input unit. According to the chosen correlation expression, measured voltage V1, and waist measurement U of the subject, the visceral fat quantity m of the subject is computed.

The body fat measuring apparatus of FIG. 17 has three or more electrodes in the first electrode group 28. Thus, in addition to measuring the voltage V1, the measuring unit of the controller 8 may measure a voltage V2 aforementioned to improve the computation accuracy of the visceral fat quantity m. In this case, the computing unit of the controller 8 may store the following correlation expression:

$$m=a0+a1 U^{n'}-(a2 \cdot V1+a3 \cdot V2) \cdot U^n, \text{ or}$$

$$m=a0+a1 U^{n'}-(a2 \cdot V1+a3 \cdot V2) \cdot U^n+b \cdot Z.$$

Figure 20:
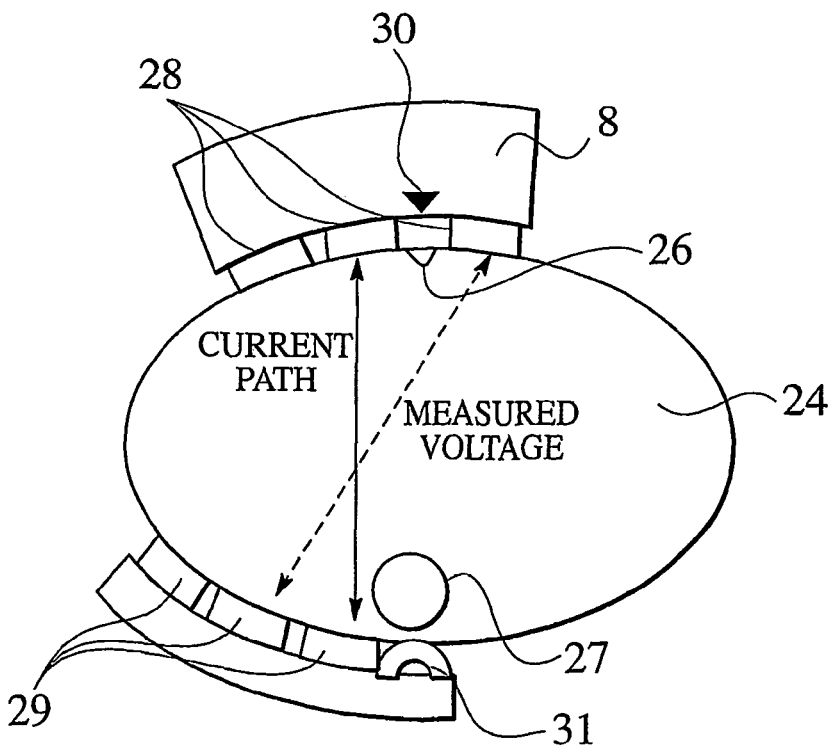

The body fat measuring apparatus of FIG. 17 includes more than two electrodes in the first electrode group 28. Thus, the measuring unit of the controller 8 may supply a current between an electrode selected from the first electrode group 28 and an electrode selected from the second electrode group 29, and measure a voltage V3 generated between a remaining electrode of the first electrode group 28 and a remaining electrode of the second electrode group 29, to improve the computation accuracy of the visceral fat quantity m. FIG. 20 shows an example of a current path to measure the voltage V3. In this case, a correlation expression stored in the computing unit may be as follows:

$$m=a0+a1 U^{n'}+(a2 \cdot V3-a3 \cdot V1) \cdot U^n, \text{ or}$$

$$m=a0+a1 U^{n'}+(a2 \cdot V3-a3 \cdot V1 a4 \cdot V2) \cdot U^n.$$

These expressions may involve an age term of "b·Z." Like the waist measurement U, the voltage V3 corresponds to a total fat quantity, and therefore, the term "a1·$U^{n'}$" may be omitted from the expressions.

The distance between the electrodes of the second electrode group 29 is set in an optimum range. The distance between two current supply electrodes is preferably shorter than ⅙, more preferably, ⅛ of the abdominal circumferential length of a subject. If the distance is too large, a current supplied between the electrodes will flow deeply inside the body of the subject, and a measured voltage V1 is affected by the distributions and quantities of muscle and visceral fat of the subject. If the distance is too short, the measuring sensitivity of the measuring unit deteriorates as the thickness of subcutaneous fat increases, and in addition, a measured voltage V1 is affected by the shapes and sizes of the electrodes. The distance between a voltage measuring electrode and the current supply electrode adjacent to the voltage measuring electrode is preferably about 0.5 to 3 times the thickness of subcutaneous fat of a subject. If this distance is too large, a contribution of a voltage drop due to the subcutaneous fat toward a measured voltage V1 becomes small, to deteriorate measuring accuracy. In addition, the large distance deteriorates the measuring sensitivity of the measuring unit on a subject having a thin subcutaneous fat layer. If the distance is too short, the measuring sensitivity of the apparatus deteriorates as the subcutaneous fat thickens, and a measured voltage V1 is affected by the shapes and sizes of the electrodes and contact states between the electrodes and the subject. If the waist measurement of a subject is 60 to 90 cm and the thickness of subcutaneous fat of the subject is 1 to 4 cm, it is preferable to set the distance (center-to-center distance) between current supply electrodes to 1 to 15 cm, more preferably, 2 to 10 cm. It is also preferable to set the distance (center-to-center distance) between a voltage measuring electrode and the current supply electrode adjacent to the voltage measuring electrode to 0.6 to 10 cm, more preferably, 1 to 6 cm. The same electrode distances are applicable to the electrodes of the first electrode group 28.

The third embodiment follows the second embodiment in regard to the posture and breathing of a subject during measurement, the characteristics of a current source and voltmeter, the shapes and materials of the electrodes, etc.

Eighth Modification

Figure 21:
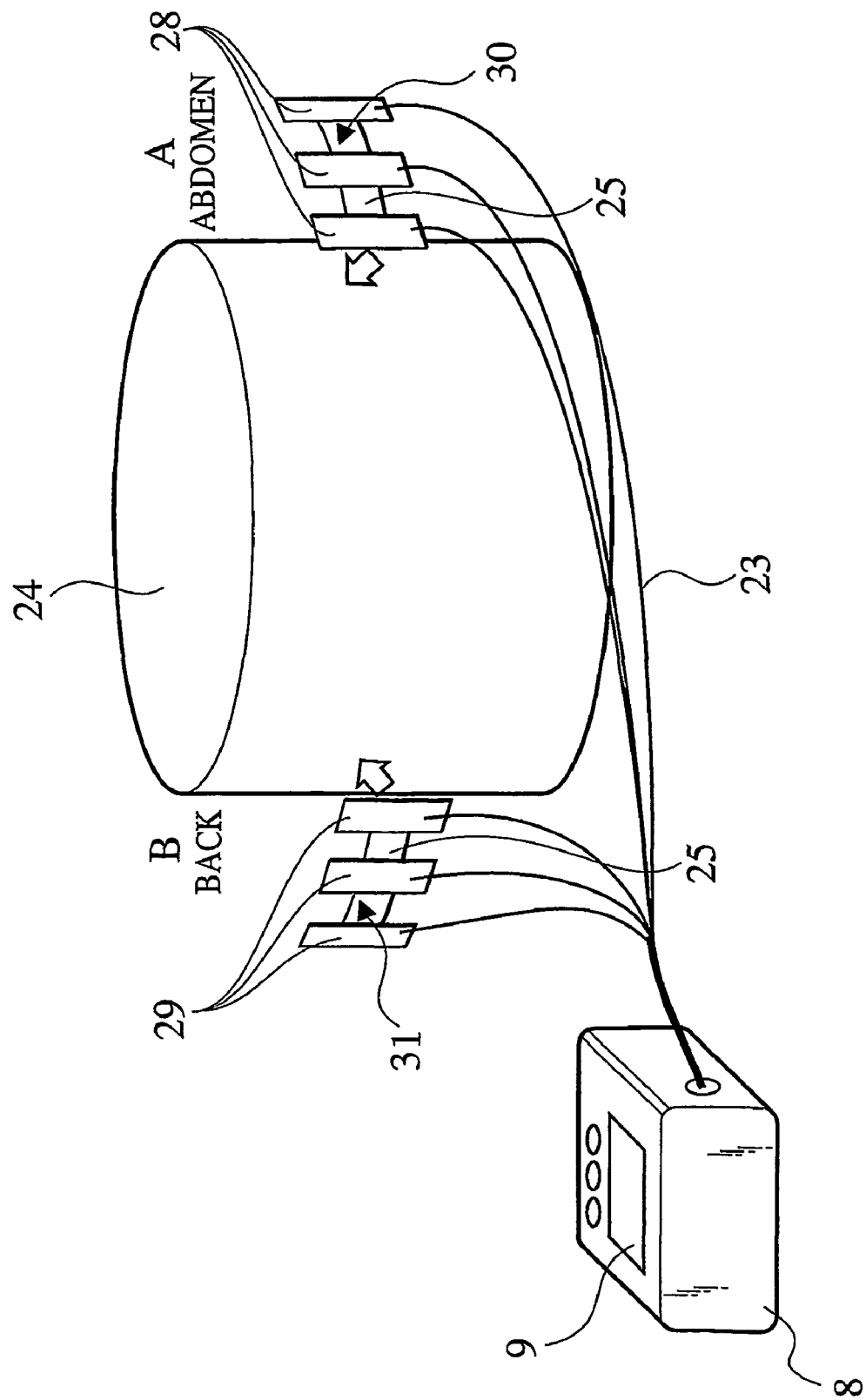
FIG. 21 shows a body fat measuring apparatus according to an eighth modification based on the third embodiment.

FIG. 21 shows a body fat measuring apparatus according to an eighth modification based on the third embodiment. The apparatus has a first electrode group 28 including three electrodes and arranged on the abdominal surface of a subject with the navel of the subject serving as a reference position, a second electrode group 29 including three electrodes and arranged on the back surface of the subject, a navel marker 30 to indicate the reference position where the first electrode group 28 is positioned, a spine marker 31 to indicate a reference position where the second electrode group 29 is positioned, a controller 8, and cords 23 to electrically connect the first and second electrode groups 28 and 29 to the controller 8. The controller 8 has a measuring unit to supply a current between two electrodes selected from the second electrode group 29 and measure a voltage generated between an electrode selected from the first electrode group 28 and an electrode selected from the second electrode group 29. The controller 8 also has a computing unit to compute a body fat quantity of the abdominal part of the subject according to the measured voltage. The controller 8 may have an input unit to enter physical data such as the circumferential length (waist measurement), sex, age (if required), etc., of the subject, and a display 9 to display the entered data and computed fat quantity. The computing unit computes the abdominal fat quantity of the subject according to the measured voltage and the data such as waist measurement, sex, and age (if required) of the subject. The first and second electrode groups 28 and 29 are attached to the surface of the subject with adhesive material or attachments such as suckers.

A method of measuring a body fat quantity with the apparatus of FIG. 21 will be explained. The navel marker 30 is aligned with the navel of a subject and the first electrode group 28 is attached to the abdominal surface of the body 24 of the subject. The spine marker 31 is aligned with the spine of the subject and the second electrode 29 is attached to the back surface of the body 24. It is preferable to equalize the attaching height of the second electrode group 29 with that of the first electrode group 28. For example, a laser pointer is used to emit a laser beam to the surface of the body 24 to confirm the height where the electrode groups are attached. The attaching height of the electrode groups is, for example, the height of the navel of the subject. The controller 8 is manipulated to enter physical data such as the waist measurement, sex, and age (if required) of the subject. A start button on the controller 8 is pushed and the measuring unit of the controller 8 supplies a current between two electrodes selected from the second electrode group 29 and measures a voltage generated between an electrode selected from the first electrode group 28 and an electrode selected from the second electrode group 29. The computing unit of the controller 8 computes an abdominal fat quantity of the subject according to the measured voltage and entered physical data. The computed fat quantity is displayed on the display 9.

One may use the apparatus to measure the body fat quantity of a third person. In this case, the body 24 of FIG. 21 is of the third person whose body fat quantity is to be measured.

Figure 22:
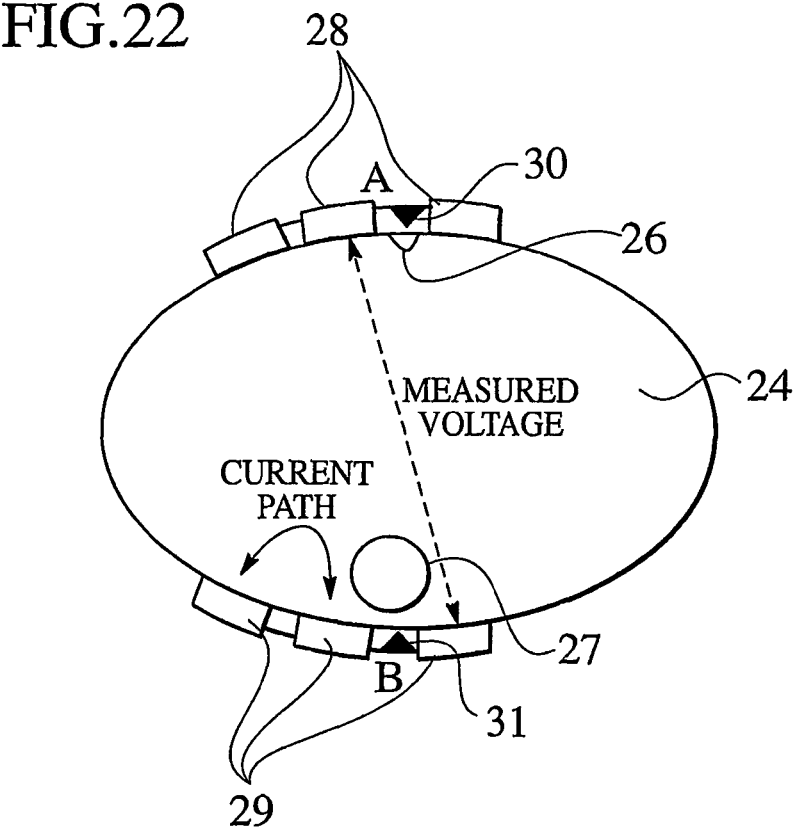
FIGS. 22 to 24 show examples of current paths formed to measure voltages according to the eighth modification.
Figure 23:
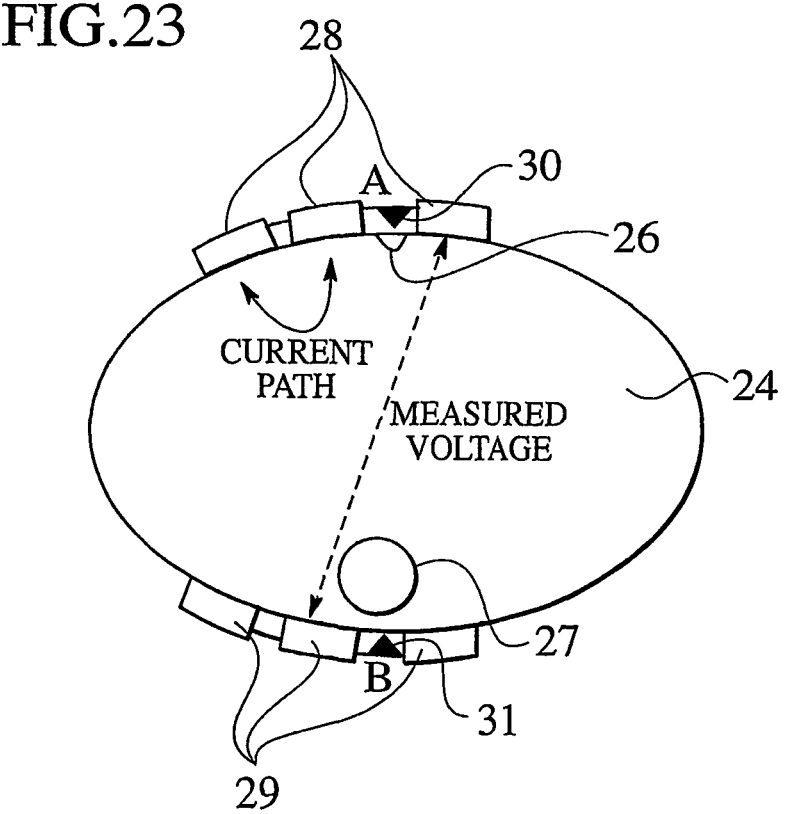
Figure 24:
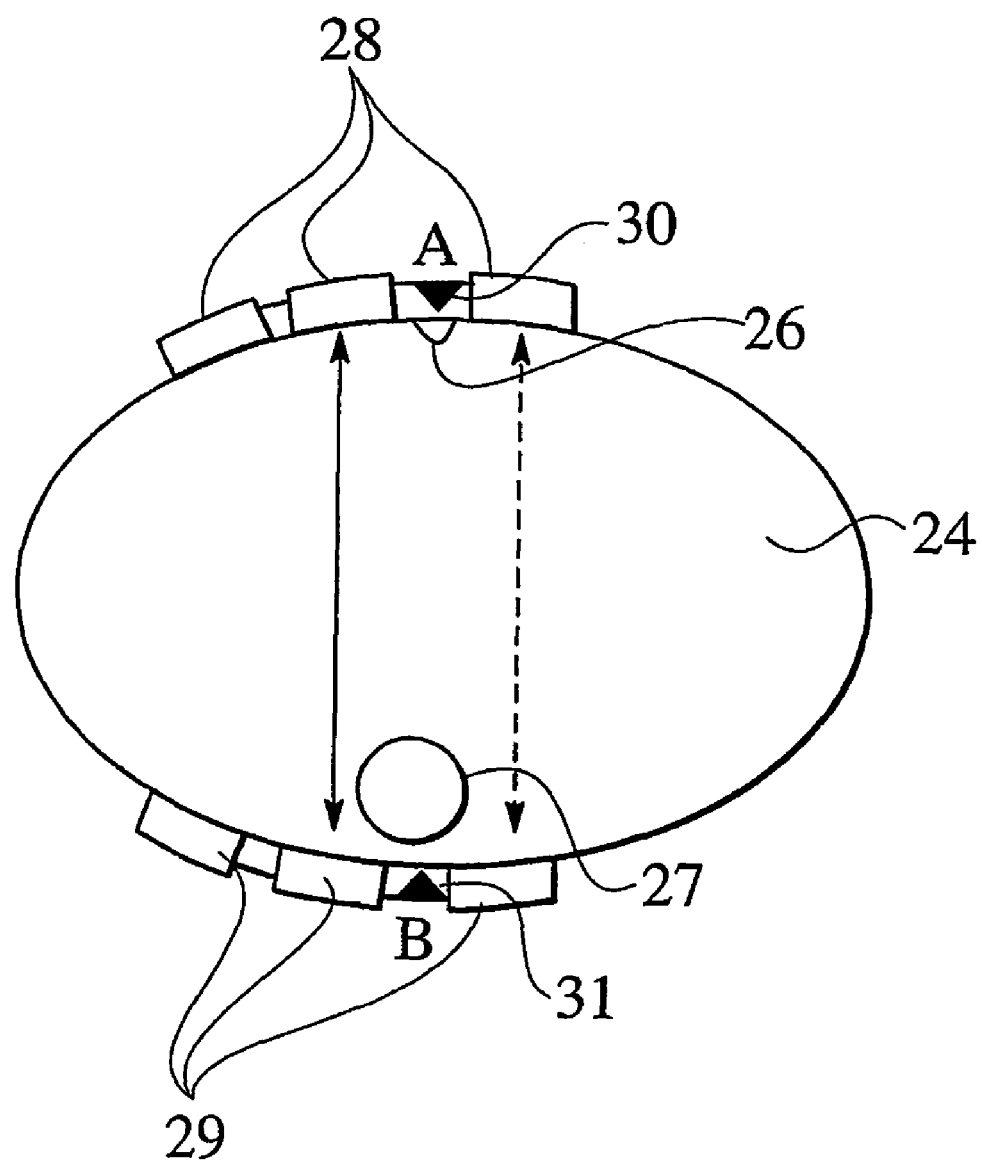

The eighth modification follows the third embodiment in regard to the measurable body fat quantities, the measuring principle, the technique of preparing correlation expressions, distances between the electrodes of the electrode groups, etc. FIGS. 22, 23, and 24 respectively show examples of current paths in the eighth modification formed to measure voltages V1, V2 and V3, which are defined in the third embodiment. The descriptions of the seventh modification according to the second embodiments concerning the structures of the electrode groups having adhesive material or attachments such as suckers are substantially applicable to the eighth modification. The eighth modification follows the second embodiment in regard to the posture and breathing of a subject during measurement, the characteristics of a current source and voltmeter, the shapes and materials of the electrodes, etc.

Figure 25:
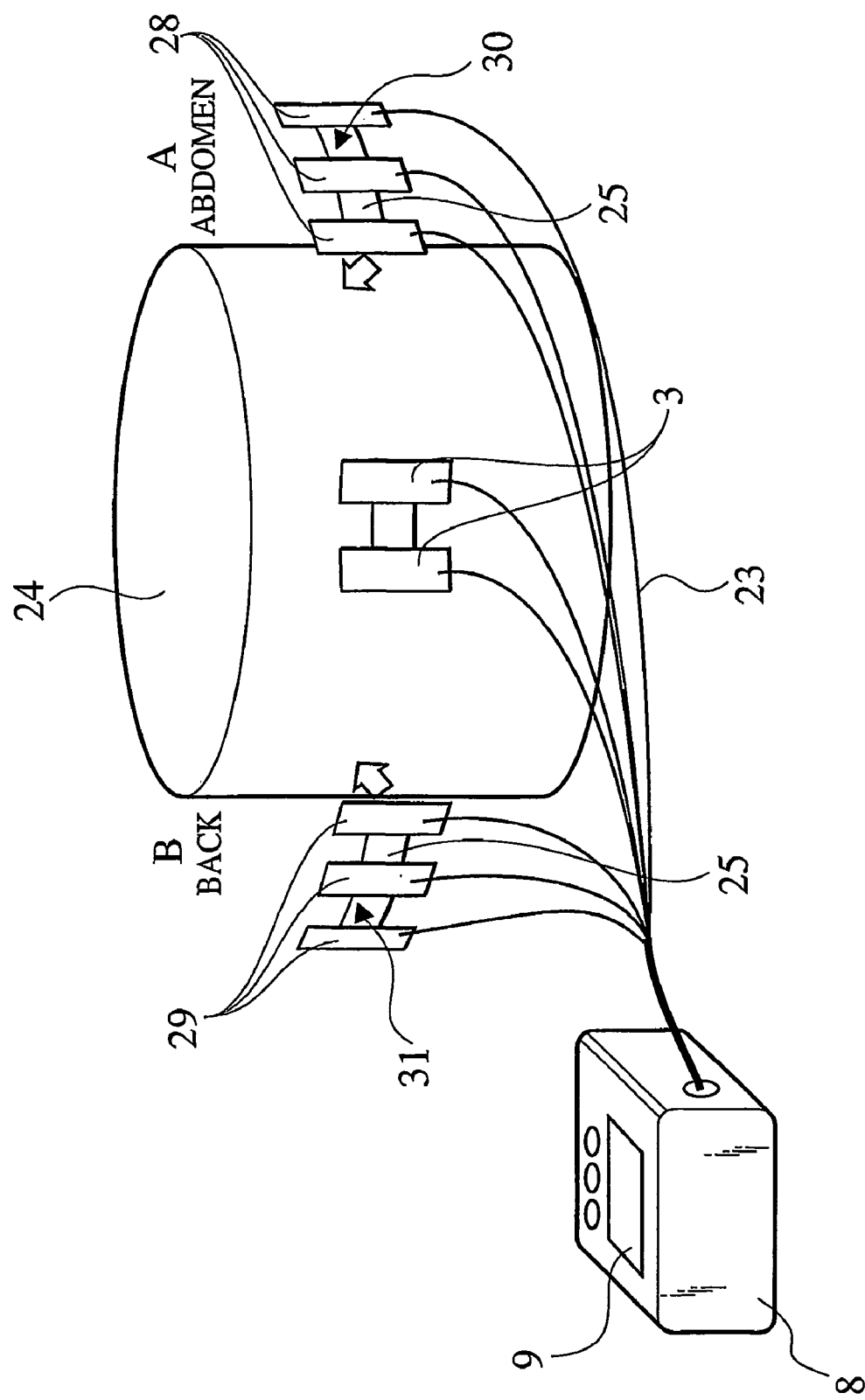
FIG. 25 shows a body fat measuring apparatus according to a combination of the seventh and eighth modifications.

A combination of the second and third embodiments of the present invention may provide another body fat measuring apparatus. FIG. 25 shows an example of a body fat measuring apparatus according to a combination of the seventh modification based on the second embodiment and the eighth modification based on the third embodiment.

In FIG. 25, a measuring unit in the controller 8 supplies a current between one of three electrodes of a first electrode group 28 and one of three electrodes of a second electrode group 29, measures a voltage V generated between two electrodes of a third electrode group 3, supplies a current between two electrodes selected from the second electrode group 29, and measures a voltage V1 generated between an electrode selected from the first electrode group 28 and an electrode selected from the second electrode group 29. A computing unit of the controller 8 computes a visceral fat quantity according to the voltage V and the method of the seventh modification according to the second embodiment, and at the same time, computes a visceral fat quantity according to the voltage V1 and the method of the eighth modification according to the third embodiment. The computed visceral fat quantities are displayed on the display 9.

Comparing the visceral fat quantities computed according to the two methods with each other improves the reliability of the fat quantity computations. If they greatly differ from each other, the display 9 may display a message to prompt a retry of measurement.

According to the present invention, body fat measurement may be made with currents of different frequencies, and measured results are compared with one another to improve the reliability of the body fat measurement.

Any one of the body fat measuring apparatuses of the second and third embodiments may take account of changes in the electric impedance of a subject (human) within a day. That is, a measured voltage may be corrected according to the time of the measurement, to correct an error in a computed body fat quantity due to hourly variations in the electric impedance of the subject. The stomach of a human body changes its state before and after a meal. Accordingly, a measured voltage may be corrected according to an elapsed time after a meal to the measurement. This corrects an error in a computed body fat quantity due to the meal. The computing unit may store a reference voltage range so that an error message is displayed on the display 9 when a measured voltage deviates from the reference voltage range owing to, for example, improper contact between the skin of a subject and electrodes.

A measured body fat quantity such as a visceral fat sectional area or a subcutaneous fat sectional area may be displayed in an absolute value in $cm^2$ or $in^2$. Alternatively, the measured fat area may be multiplied by a proper coefficient to provide a standardized value. When the fat area is displayed in $cm^2$, it may be displayed at intervals of 1 $cm^2$, $2 \text{ cm}^2$, $5 \text{ cm}^2$, $10 \text{ cm}^2$, $20 \text{ cm}^2$, etc. If large intervals such as $10 \text{ cm}^2$ and $20 \text{ cm}^2$ are employed, not only the absolute value of a fat area but also a standardized value having smaller intervals or a measured voltage may simultaneously be displayed to sensitively indicate the change of a fat quantity. The same is applicable when displaying a measured fat quantity in inches. A measured body fat quantity may be correlated to and transformed into a body fat ratio used for conventional body fat meters and be displayed on the display 9 in the form of the body fat ratio. There is a medical view that visceral fat causes lifestyle-related illnesses such as hyperlipemia, diabetes, hypertension, etc. Hence health advice may be displayed on the display 9 on the basis of a measured visceral fat quantity.

As explained above, the body fat measuring apparatus according to the present invention is easy to apply to a subject and is capable of easily and accurately measuring a subcutaneous fat quantity such as the thickness or sectional area of a subcutaneous fat layer and a visceral fat quantity of the subject.

This application claims benefit of priority under 35USC §119 to Japanese Patent Applications No. 2001-046661, filed on Feb. 22, 2001, No. 2001-115607, filed on Apr. 13, 2001, and No. 2001-206937, filed on Jul. 6, 2001, the entire contents of which are incorporated by reference herein. Although the invention has been described above by reference to certain embodiments of the invention, the invention is not limited to the embodiments described above. Modifications and variations of the embodiments described above will occur to those skilled in the art, in light of the teachings. The scope of the invention is defined with reference to the following claims.

The invention claimed is:

1. An apparatus for measuring body fat, comprising:
a first electrode group including at least an electrode and configured to be arranged on the abdominal surface of a subject with the navel of the subject serving as a reference position;
a second electrode group including at least an electrode and configured to be arranged on the back surface of the subject;
a third electrode group including at least two electrodes and configured to be arranged on one side of the surface of the subject at an intermediate position between the first and second electrode groups;
a measuring unit configured to measure a voltage generated between predetermined two electrodes of the third electrode group, the voltage being generated in response to a current supplied between an electrode selected from the first electrode group and an electrode selected from the second electrode group; and
a computing unit configured to compute an abdominal fat quantity of the subject according to the measured voltage.

2. The apparatus of claim 1, further comprising
an input unit to enter a circumferential length of the abdominal part of the subject,
the computing unit computing an abdominal fat quantity of the subject according to the measured voltage and entered circumferential length.

3. The apparatus of claim 2, wherein:
the first, second, and third electrode groups are installed on a belt that is substantially inelastic; and
a distance between the first and third electrode groups is substantially equal to a distance between the third and second electrode groups.

4. The apparatus of claim 2, wherein:
the first, second, and third electrode groups are installed on a belt that is elastic; and
distances between the electrode groups are adjustable due to the elasticity of the belt.

5. The apparatus of claim 2, wherein:
the first, second, and third electrode groups are installed on a belt that is substantially inelastic; and
the belt has adjusters to adjust distances between the electrode groups.

6. The apparatus of claim 2, further comprising joints connecting the first and third electrode groups to each other and the second and third electrode groups to each other.

7. The apparatus of claim 2, further comprising attachments configured to attach the first, second, and third electrode groups to the surface of the subject.

8. The apparatus of claim 1, wherein the second electrode group is positioned on the back surface of the subject relative to a spine of the subject.

9. The apparatus of claim 1, wherein:
the first, second, and third electrode groups are installed on a belt that is substantially inelastic; and
a distance between the first and third electrode groups is substantially equal to a distance between the third and second electrode groups.

10. The apparatus of claim 1, wherein:
the first, second, and third electrode groups are installed on a belt that is elastic; and
distances between the electrode groups are adjustable due to the elasticity of the belt.

11. The apparatus of claim 1, wherein:
the first, second, and third electrode groups are installed on a belt that is substantially inelastic; and
the belt has adjusters to adjust distances between the electrode groups.

12. The apparatus of claim 1, further comprising joints connecting the first and third electrode groups to each other and the second and third electrode groups to each other.

13. The apparatus of claim 1, further comprising attachments configured to attach the first, second, and third electrode groups to the surface of the subject.

14. The apparatus of claim 1, wherein the abdominal fat quantity is a visceral fat quantity.

15. The apparatus of claim 1, wherein the computing unit is configured to compute the abdominal fat quantity on the basis of a polynomial function of the measured voltage.

16. An apparatus for measuring body fat, comprising:
a first electrode group including at least one electrode and configured to be arranged on the abdominal surface of a subject;
a second electrode group including at least one electrode and configured to be arranged on the back surface of the subject;
a third electrode group including at least two electrodes and configured to be arranged on one side of the surface of the subject at an intermediate position between the first and second electrode groups;
a measuring unit configured to measure a voltage generated between predetermined two electrodes of the third electrode group, the voltage being generated in response to a current supplied between an electrode selected from the first electrode group and an electrode selected from the second electrode group;
an input unit configured for a subject to enter a circumferential length of the abdominal part of the subject, the sex of the subject; and a computing unit configured to compute a visceral fat quantity of the subject according to the measured voltage and the entered circumferential length, and sex of the subject.

17. The apparatus of claim 16, wherein the computing unit is configured to compute an visceral fat quantity on the basis of a polynomial function of the measured voltage.

18. A belt for measuring body fat, comprising:
a navel marker configured to be aligned with the navel of a subject;
a first electrode group including at least an electrode and configured to be arranged on the abdominal surface of the subject with the navel marker being aligned with the navel of the subject;
a second electrode group including at least an electrode and configured to be arranged on the back surface of the subject; and
a third electrode group including at least two electrodes and configured to be arranged on one side of the surface of the subject at an intermediate position between the first and second electrode groups and configured to measure a voltage drop generated as current passes from an electrode of the first group to an electrode of the second group.

19. The belt of claim 18, further comprising a computing unit configured to compute the abdominal fat quantity on the basis of a polynomial function of the measured voltage.

20. The belt of claim 18, further comprising:
a current source circuit to supply a current between an electrode selected from the first electrode group and an electrode selected from the second electrode group;
a voltage measuring circuit configured to measure a voltage generated between predetermined two electrodes of the third electrode group; and
a computing circuit to compute an abdominal fat quantity of the subject according to the measured voltage.

21. The belt of claim 18, further comprising
an input unit to enter a circumferential length of the abdominal part of the subject, the computing circuit computing an abdominal fat quantity of the subject according to the measured voltage and entered circumferential length.

22. The belt of claim 20, further comprising
a transmit/receive circuit configured to communicate with a control unit separated from the belt, the transmit/receive circuit transmitting information related to the computed fat quantity and receiving information related to voltage measurement.

23. An apparatus for measuring body fat, comprising:
a first electrode group including at least an electrode and configured to be arranged on the abdominal surface of a subject with the navel of the subject serving as a reference position;
a second electrode group including at least three electrodes and configured to be arranged on the back surface of the subject;
a measuring unit configured to supply a current between two electrodes selected from the second electrode group and measure a voltage generated between an electrode selected from the first electrode group and an electrode selected from the second electrode group; and
a computing unit configured to compute an abdominal fat quantity of the subject according to the measured voltage and a circumferential length of the abdominal part of the subject.

24. The apparatus of claim 23, further comprising
an input unit to enter a circumferential length of the abdominal part of the subject,
the computing unit computing an abdominal fat quantity according to the measured voltage and entered circumferential length.

25. The apparatus of claim 23, wherein the second electrode group is positioned on the back surface of the subject relative to a spine of the subject.

26. The apparatus of claim 23, further comprising a joint to connect the first and second electrode groups to each other.

27. The apparatus of claim 23, further comprising attachments to attach the electrodes of the first and second electrode groups to the surface of the subject.

28. The apparatus of claim 23, wherein the abdominal fat quantity is a visceral fat quantity or a subcutaneous fat quantity.

29. The apparatus of claim 23, wherein the computing unit is configured to compute the abdominal fat quantity on the basis of a polynomial function of the measured voltage and the circumferential length.

30. An apparatus for measuring body fat, comprising:
a first electrode group including at least an electrode and configured to be arranged on the abdominal surface of the subject with the navel of the subject serving as a reference position;
a second electrode group including at least three electrodes and configured to be arranged on the back surface of the subject;
a measuring unit configured to supply a current between two electrodes selected from the second electrode group and measure a voltage generated between an electrode selected from the first electrode group and an electrode selected from the second electrode group;
an input unit configured for a subject to enter a circumferential length of the abdominal part of the subject and the sex of the subject; and
a computing unit configured to compute a visceral fat quantity of the subject according to the measured voltage and the entered circumferential length and sex of the subject.

31. The apparatus of claim 30 further comprising an input unit to enter the age of the subject.

32. The apparatus of claim 30, wherein the input is configured to accept an input defining an age of the subject, and the computing unit is configured to compute the visceral fat quantity of the subject based in part on an entered age of the subject.

33. The apparatus of claim 30, wherein the computing unit is configured to compute the visceral fat quantity on the basis of a polynomial function of the measured voltage and the entered circumferential length and a sex of the subject.

34. An apparatus for measuring body fat, comprising:
two current supply electrodes configured to be arranged on the circumferential surface of a subject with the distance between the electrodes being sufficiently shorter than a circumferential length of the subject;
a first measuring electrode configured to be arranged on the subject in the vicinity of one of the current supply electrodes;
a second measuring electrode configured to be arranged on the subject substantially opposite to the current supply electrodes across the subject;

a voltage measuring unit configured to supply a current between the current supply electrodes and measure a voltage generated between the first and second measuring electrodes; and a computing unit configured to compute a visceral fat quantity of the subject according to the measured voltage and a characteristic quantity representing the size of the subject.

35. The apparatus of claim 34, wherein the computing unit is configured to compute the visceral fat quantity on the basis of a polynomial function of the measured voltage and the characteristic quantity.

36. An apparatus for measuring body fat, comprising:

two current supply electrodes configured to be arranged on the circumferential surface of a subject with the distance between the electrodes being sufficiently shorter than a circumferential length of the subject;

two measuring electrodes each configured to be arranged on the subject in the vicinities of the current supply electrodes;

a voltage measuring unit configured to supply a current between the current supply electrodes and measure a voltage generated between the measuring electrodes; and a computing unit configured to compute a visceral fat quantity of the subject according to the measured voltage and a characteristic quantity representing a circumference of the subject.

37. The apparatus of claim 36, wherein the computing unit is configured to compute the visceral fat quantity on the basis of a polynomial function of the measured voltage and the characteristic quantity.

38. An apparatus for measuring body fat, comprising:

two current supply electrodes configured to be arranged on the circumferential surface of a subject substantially opposite to each other across the subject;

two measuring electrodes configured to be arranged in the vicinity of one of the current supply electrodes with the distance between the measuring electrodes being sufficiently shorter than a circumferential length of the subject;

a measuring unit configured to supply a current between the current supply electrodes and measure a voltage generated between the measuring electrodes; and a computing unit configured to compute a visceral fat quantity of the subject according to the measured voltage and a characteristic quantity representing the size of the subject.

39. The apparatus of claim 38, wherein the computing unit is configured to compute the visceral fat quantity on the basis of a polynomial function of the measured voltage and the characteristic quantity.

* * * * *